United States Patent
Enerbäck et al.

(10) Patent No.: US 6,709,860 B1
(45) Date of Patent: Mar. 23, 2004

(54) ANIMAL MODEL

(75) Inventors: Sven Enerbäck, Mölndal (SE); Peter Carlsson, Floda (SE)

(73) Assignee: Biovitrum AB, Stockholm (SE)

( * ) Notice: Subject to any disclaimer, the term of this patent is extended or adjusted under 35 U.S.C. 154(b) by 169 days.

(21) Appl. No.: 09/587,945

(22) Filed: Jun. 6, 2000

Related U.S. Application Data

(63) Continuation-in-part of application No. 09/085,380, filed on May 26, 1998, now abandoned.
(60) Provisional application No. 60/190,692, filed on Mar. 20, 2000.

(30) Foreign Application Priority Data

May 26, 1997  (SE) .............................................. 9701963

(51) Int. Cl.$^7$ ......................... C07H 21/04; C12N 15/00
(52) U.S. Cl. ................... 435/320.1; 536/23.1; 536/23.5
(58) Field of Search ...................... 435/320.1; 536/23.1, 536/23.5

(56) References Cited

FOREIGN PATENT DOCUMENTS

WO          WO9530026          11/1995

OTHER PUBLICATIONS

Miura et al, Genomics, 41:489–492 (1997).
Miura et al, FEBS Letters 326 (1,2,3): 171–176 (Jul. 1993).
Enerbäck et al, Molecular and Cellular Biology 12 (10): 4622–4633 (Oct. 1992).
M/S Synthèse Médecine/sciences 12: 885–90 (1996).

*Primary Examiner*—Sean McGarry
(74) *Attorney, Agent, or Firm*—Fish & Richardson P.C.

(57) ABSTRACT

According to the invention, a major role for the winged helix protein FKHL14/FOXC2 in regulating energy balance and adiposity is demonstrated. The invention relates to transgenic non-human mammalian animals being capable of expressing the human FKHL14/FOXC2 gene in its adipose tissue. The invention also relates to methods for identifying compounds useful for the treatment of medical conditions related to obesity or diabetes, said compounds being capable of stimulating expression of the human FKHL14/FOXC2 gene, or being capable of stimulating the biological activity of a polypeptide encoded by the human FKHL14/FOXC2 gene. The invention further relates to methods for identifying compounds useful for the treatment of medical conditions related to malnutrition, said compounds being capable of decreasing expression of the human FKHL14/FOXC2 gene, or being capable of decreasing the biological activity of a polypeptide encoded by the human FKHL14/FOXC2 gene.

13 Claims, 16 Drawing Sheets

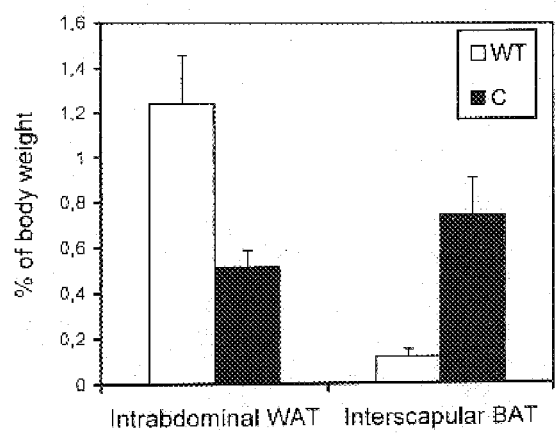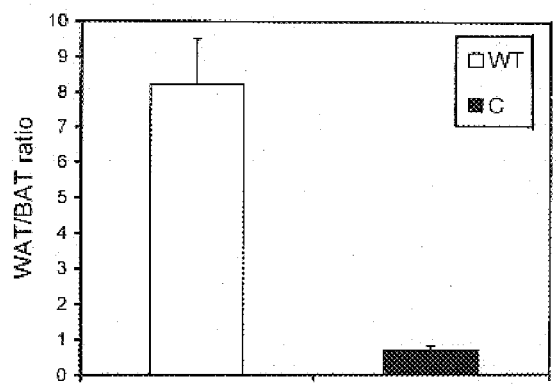
FIG. 9A
FIG. 9B

SEQUENCE LISTING

```
<160> NUMBER OF SEQ ID NOS:  26

<210> SEQ ID NO 1
<211> LENGTH: 3289
<212> TYPE: DNA
<213> ORGANISM: Homo sapiens
<220> FEATURE:
<221> NAME/KEY: CDS
<222> LOCATION: (1197)..(2702)
<300> PUBLICATION INFORMATION:
<300> PUBLICATION INFORMATION:
<303> JOURNAL: Genomics
<304> VOLUME: 41
<306> PAGES: 489-492
<307> DATE: 1997
<308> DATABASE ACCESSION NUMBER: GenBank/Y08223
<309> DATABASE ENTRY DATE: 1997-05-14
<313> RELEVANT RESIDUES: 1 TO 3289

<400> SEQUENCE: 1
gaattcggag gattaagttg tcagtcagca cgttgctacc ttcccctcta tgcactccgc      60
tgcctggctc ctcggcgggg agcgagggaa actcagtttg tagggtttac ctctaaaacc     120
tcgataggtt atccttgacg accccgagcc tggaaactcc ctgttgatga ttaattattt     180
gattaaataa gtataacatc caggagaggc cctgccattc caatccagcg cgtttgcttt     240
tgaatccatt acacctgggc ccccataatt aggaaatcta attattcgct tcatcactca     300
ttaataagaa aaatgtccca ggatcattgc tacttacaag gtctttggga gagatatttt     360
actctattaa tccattctat tttatatttc aaattgattt tttttaacag aggaaagtgg     420
ctatcttttt gttttgggca tgtgggccca ttcaccaaaa tgtgatcata aaataaattt     480
taataagata taactttta aaaagttttc aagtgaagac ggagtcgccg cggaggccgg     540
ggcggcgggg tcttagagcc gacggattcc tgcgctcctc gccccgattg gcgccggact     600
cctctcagct gccgggtgat tggctcaaag ttccgggagg gggcgtggcc cgaggaaagt     660
aaaaactcgc tttcagcaag aagacttttg aaactttttcc caatccctaa aagggacttg     720
gcctcttttt ctgggctcag cggggcagcc gctcggaccc cggcgcgctg accctcgggg     780
ctgccgattc gctgggggct tggagagcct cctgcgcccc tcctcgcgcg ggccgagggt     840
ccaccttggt ccccaggccg cggcgtctcc gctgggtccg cggccgcccg cctgcccgcg     900
```

```
ctgccgccgc cgggtcctgg agccagcgag gagcggggcc ggcgctgcgc ttgcccgggg     960
cgcgccctcc aggatgccga tccgcccggt ccgctgaaag cgcgcgcccc tgctcggccc    1020
gagcgacgac gaccgcgcac cctcgccccg gaggctgcca ggagaccggg gccgcccctc    1080
ccgctcccct cctctccccc tctggctctc tcgcgctctc tcgctctcag ggccccctc    1140 gctccccgg ccgcagtccg tgcgcgaggg cgccggcgag ccgtctcgga agcagc atg    1199
                                                             Met
                                                              1 cag gcg cgc tac tcc gtg tcc gac ccc aac gcc ctg gga gtg gtg ccc    1247
Gln Ala Arg Tyr Ser Val Ser Asp Pro Asn Ala Leu Gly Val Val Pro
          5                  10                  15 tac ctg agc gag cag aat tac tac cgg gct gcg ggc agc tac ggc ggc    1295
Tyr Leu Ser Glu Gln Asn Tyr Tyr Arg Ala Ala Gly Ser Tyr Gly Gly
     20                  25                  30 atg gcc agc ccc atg ggc gtc tat tcc ggc cac ccg gag cag tac agc    1343
Met Ala Ser Pro Met Gly Val Tyr Ser Gly His Pro Glu Gln Tyr Ser
 35                  40                  45 gcg ggg atg ggc cgc tcc tac gcg ccc tac cac cac cag ccc gcg        1391
Ala Gly Met Gly Arg Ser Tyr Ala Pro Tyr His His His Gln Pro Ala
 50                  55                  60                  65 gcg cct aag gac ctg gtg aag ccg ccc tac agc tac atc gcg ctc atc    1439
Ala Pro Lys Asp Leu Val Lys Pro Pro Tyr Ser Tyr Ile Ala Leu Ile
             70                  75                  80 acc atg gcc atc cag aac gcg ccc gag aag aag atc acc ttg aac ggc    1487
Thr Met Ala Ile Gln Asn Ala Pro Glu Lys Lys Ile Thr Leu Asn Gly
         85                  90                  95 atc tac cag ttc atc atg gac cgc ttc ccc ttc tac cgg gag aac aag    1535
Ile Tyr Gln Phe Ile Met Asp Arg Phe Pro Phe Tyr Arg Glu Asn Lys
    100                 105                 110 cag ggc tgg cag aac agc atc cgc cac aac ctc tcg ctc aac gag tgc    1583
Gln Gly Trp Gln Asn Ser Ile Arg His Asn Leu Ser Leu Asn Glu Cys
115                 120                 125 ttc gtc aag gtg ccc cgc gac gac aag aag ccc ggc aag ggc agt tac    1631
Phe Val Lys Val Pro Arg Asp Asp Lys Lys Pro Gly Lys Gly Ser Tyr
130                 135                 140                 145 tgg acc ctg gac ccg gac tcc tac aac atg ttc gag aac ggc agc ttc    1679
Trp Thr Leu Asp Pro Asp Ser Tyr Asn Met Phe Glu Asn Gly Ser Phe
            150                 155                 160 ctg cgg cgc cgg cgg cgc ttc aaa aag aag gac gtg tcc aag gag aag    1727
Leu Arg Arg Arg Arg Arg Phe Lys Lys Lys Asp Val Ser Lys Glu Lys
        165                 170                 175 gag gag cgg gcc cac ctc aag gag ccg ccc ccg gcg gcg tcc aag ggc    1775
Glu Glu Arg Ala His Leu Lys Glu Pro Pro Pro Ala Ala Ser Lys Gly
    180                 185                 190 gcc ccg gcc acc ccc cac cta gcg gac gcc ccc aag gag gcc gag aag    1823
Ala Pro Ala Thr Pro His Leu Ala Asp Ala Pro Lys Glu Ala Glu Lys
195                 200                 205 aag gtg gtg atc aag agc gag gcg gcg tcc ccg gcg ctg ccg gtc atc    1871
Lys Val Val Ile Lys Ser Glu Ala Ala Ser Pro Ala Leu Pro Val Ile
210                 215                 220                 225 acc aag gtg gag acg ctg agc ccc gag agc gcg ctg cag ggc agc ccg    1919
Thr Lys Val Glu Thr Leu Ser Pro Glu Ser Ala Leu Gln Gly Ser Pro
            230                 235                 240 cgc agc gcg gcc tcc acg ccc gcc ggc tcc ccc gac ggt tcg ctg ccg    1967
Arg Ser Ala Ala Ser Thr Pro Ala Gly Ser Pro Asp Gly Ser Leu Pro
        245                 250                 255 gag cac cac gcc gcg gcg ccc aac ggg ctg cct ggc ttc agc gtg gag    2015
Glu His His Ala Ala Ala Pro Asn Gly Leu Pro Gly Phe Ser Val Glu
    260                 265                 270
```

-continued

```
aac atc atg acc ctg cga acg tcg ccg ccg ggc gga gag ctg agc ccg    2063
Asn Ile Met Thr Leu Arg Thr Ser Pro Pro Gly Gly Glu Leu Ser Pro
    275                 280                 285 ggg gcc gga cgc gcg ggc ctg gtg gtg ccg ccg ctg gcg ctg cca tac    2111
Gly Ala Gly Arg Ala Gly Leu Val Val Pro Pro Leu Ala Leu Pro Tyr
290                 295                 300                 305 gcc gcc gcg ccc ccc gcc gcc tac ggc cag ccg tgc gct cag ggc ctg    2159
Ala Ala Ala Pro Pro Ala Ala Tyr Gly Gln Pro Cys Ala Gln Gly Leu
                310                 315                 320 gag gcc ggg gcc gcc ggg ggc tac cag tgc agc atg cga gcg atg agc    2207
Glu Ala Gly Ala Ala Gly Gly Tyr Gln Cys Ser Met Arg Ala Met Ser
            325                 330                 335 ctg tac acc ggg gcc gag cgg ccg gcg cac atg tgc gtc ccg ccc gcc    2255
Leu Tyr Thr Gly Ala Glu Arg Pro Ala His Met Cys Val Pro Pro Ala
        340                 345                 350 ctg gac gag gcc ctc tcg gac cac ccg agc ggc ccc acg tcg ccc ctg    2303
Leu Asp Glu Ala Leu Ser Asp His Pro Ser Gly Pro Thr Ser Pro Leu
    355                 360                 365 agc gct ctc aac ctc gcc gcc ggc cag gag ggc gcg ctc gcc gcc acg    2351
Ser Ala Leu Asn Leu Ala Ala Gly Gln Glu Gly Ala Leu Ala Ala Thr
370                 375                 380                 385 ggc cac cac cac cag cac cac ggc cac cac cac ccg cag gcg ccg ccg    2399
Gly His His His Gln His His Gly His His His Pro Gln Ala Pro Pro
                390                 395                 400 ccc ccg ccg gct ccc cag ccc cag ccg acg ccg cag ccc ggg gcc gcc    2447
Pro Pro Pro Ala Pro Gln Pro Gln Pro Thr Pro Gln Pro Gly Ala Ala
            405                 410                 415 gcg gcg cag gcg gcc tcc tgg tat ctc aac cac agc ggg gac ctg aac    2495
Ala Ala Gln Ala Ala Ser Trp Tyr Leu Asn His Ser Gly Asp Leu Asn
        420                 425                 430 cac ctc ccc ggc cac acg ttc gcg gcc cag cag caa act ttc ccc aac    2543
His Leu Pro Gly His Thr Phe Ala Ala Gln Gln Gln Thr Phe Pro Asn
    435                 440                 445 gtg cgg gag atg ttc aac tcc cac cgg ctg ggg att gag aac tcg acc    2591
Val Arg Glu Met Phe Asn Ser His Arg Leu Gly Ile Glu Asn Ser Thr
450                 455                 460                 465 ctc ggg gag tcc cag gtg agt ggc aat gcc agc tgc cag ctg ccc tac    2639
Leu Gly Glu Ser Gln Val Ser Gly Asn Ala Ser Cys Gln Leu Pro Tyr
                470                 475                 480 aga tcc acg ccg cct ctc tat cgc cac gca gcc ccc tac tcc tac gac    2687
Arg Ser Thr Pro Pro Leu Tyr Arg His Ala Ala Pro Tyr Ser Tyr Asp
            485                 490                 495 tgc acg aaa tac tga cgtgtcccgg gacctcccct ccccggcccg ctccggcttc    2742
Cys Thr Lys Tyr
            500 gcttcccagc cccgacccaa ccagacaatt aaggggctgc agagacgcaa aaaagaaaca   2802 aaacatgtcc accaacctttt tctcagaccc gggagcagag agcgggcacg ctagccccca   2862 gccgtctgtg aagagcgcag gtaactttaa ttcgccgccc cgtttctggg atcccaggaa   2922 accccctccaa agggacgcag cccaacaaaa tgagtattgg tcttaaaatc cccctcccct   2982 accaggacgg ctgtgctgtg ctcgacctga gctttcaaaa gttaagttat ggacccaaat   3042 cccatagcga gccctagtg actttctgta ggggtcccca taggtgtatg ggggtctcta   3102 tagataatat atgtgctgtg tgtaatttta aatttctcca accgtgctgt acaaatgtgt   3162 ggatttgtaa tcaggctatt ttgttgttgt tgttgttgtt cagagccatt aatataatat   3222 ttaaagttga gttcactgga taagttttttc atcttgccca accatttcta actgccaaat   3282
```

```
tgaattc                                                                    3289
```

<210> SEQ ID NO 2
<211> LENGTH: 501
<212> TYPE: PRT
<213> ORGANISM: Homo sapiens

<400> SEQUENCE: 2

```
Met Gln Ala Arg Tyr Ser Val Ser Asp Pro Asn Ala Leu Gly Val Val
 1               5                  10                  15

Pro Tyr Leu Ser Glu Gln Asn Tyr Tyr Arg Ala Ala Gly Ser Tyr Gly
             20                  25                  30

Gly Met Ala Ser Pro Met Gly Val Tyr Ser Gly His Pro Glu Gln Tyr
         35                  40                  45

Ser Ala Gly Met Gly Arg Ser Tyr Ala Pro Tyr His His Gln Pro
     50                  55                  60

Ala Ala Pro Lys Asp Leu Val Lys Pro Pro Tyr Ser Tyr Ile Ala Leu
 65                  70                  75                  80

Ile Thr Met Ala Ile Gln Asn Ala Pro Glu Lys Lys Ile Thr Leu Asn
                 85                  90                  95

Gly Ile Tyr Gln Phe Ile Met Asp Arg Phe Pro Phe Tyr Arg Glu Asn
            100                 105                 110

Lys Gln Gly Trp Gln Asn Ser Ile Arg His Asn Leu Ser Leu Asn Glu
        115                 120                 125

Cys Phe Val Lys Val Pro Arg Asp Asp Lys Lys Pro Gly Lys Gly Ser
    130                 135                 140

Tyr Trp Thr Leu Asp Pro Asp Ser Tyr Asn Met Phe Glu Asn Gly Ser
145                 150                 155                 160

Phe Leu Arg Arg Arg Arg Arg Phe Lys Lys Lys Asp Val Ser Lys Glu
                165                 170                 175

Lys Glu Glu Arg Ala His Leu Lys Glu Pro Pro Ala Ala Ser Lys
            180                 185                 190

Gly Ala Pro Ala Thr Pro His Leu Ala Asp Ala Pro Lys Glu Ala Glu
        195                 200                 205

Lys Lys Val Val Ile Lys Ser Glu Ala Ala Ser Pro Ala Leu Pro Val
    210                 215                 220

Ile Thr Lys Val Glu Thr Leu Ser Pro Glu Ser Ala Leu Gln Gly Ser
225                 230                 235                 240

Pro Arg Ser Ala Ala Ser Thr Pro Ala Gly Ser Pro Asp Gly Ser Leu
                245                 250                 255

Pro Glu His His Ala Ala Ala Pro Asn Gly Leu Pro Gly Phe Ser Val
            260                 265                 270

Glu Asn Ile Met Thr Leu Arg Thr Ser Pro Pro Gly Gly Glu Leu Ser
        275                 280                 285

Pro Gly Ala Gly Arg Ala Gly Leu Val Val Pro Pro Leu Ala Leu Pro
    290                 295                 300

Tyr Ala Ala Ala Pro Pro Ala Tyr Gly Gln Pro Cys Ala Gln Gly
305                 310                 315                 320

Leu Glu Ala Gly Ala Ala Gly Gly Tyr Gln Cys Ser Met Arg Ala Met
                325                 330                 335

Ser Leu Tyr Thr Gly Ala Glu Arg Pro Ala His Met Cys Val Pro Pro
            340                 345                 350

Ala Leu Asp Glu Ala Leu Ser Asp His Pro Ser Gly Pro Thr Ser Pro
        355                 360                 365
```

-continued

```
Leu Ser Ala Leu Asn Leu Ala Ala Gly Gln Glu Gly Ala Leu Ala Ala
        370                 375                 380
Thr Gly His His His Gln His His Gly His His His Pro Gln Ala Pro
385                 390                 395                 400
Pro Pro Pro Pro Ala Pro Gln Pro Gln Pro Thr Pro Gln Pro Gly Ala
                405                 410                 415
Ala Ala Ala Gln Ala Ala Ser Trp Tyr Leu Asn His Ser Gly Asp Leu
            420                 425                 430
Asn His Leu Pro Gly His Thr Phe Ala Ala Gln Gln Gln Thr Phe Pro
        435                 440                 445
Asn Val Arg Glu Met Phe Asn Ser His Arg Leu Gly Ile Glu Asn Ser
    450                 455                 460
Thr Leu Gly Glu Ser Gln Val Ser Gly Asn Ala Ser Cys Gln Leu Pro
465                 470                 475                 480
Tyr Arg Ser Thr Pro Pro Leu Tyr Arg His Ala Ala Pro Tyr Ser Tyr
                485                 490                 495
Asp Cys Thr Lys Tyr
            500

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: 5 'primer

<400> SEQUENCE: 3
gcttcgcctc ctccatggga a                                         21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: 3' primer

<400> SEQUENCE: 4
ggttacaaat ccgcactcgt t                                         21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: 5' primer

<400> SEQUENCE: 5
ctcctgtgct gcagcctttc tc                                        22

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: 3' primer

<400> SEQUENCE: 6
cgtaactcac caccaccagc ttgtc                                     25

<210> SEQ ID NO 7
<211> LENGTH: 20
<212> TYPE: DNA
```

```
<213> ORGANISM: Artificial Sequence
<220> FEATURE:
<223> OTHER INFORMATION: Description of Artificial Sequence: 5' primer

<400> SEQUENCE: 7
gccaactctc ctgagagctt                                                    20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: 3' primer

<400> SEQUENCE: 8
ctcctgcttg agcttctggt t                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: 5' primer

<400> SEQUENCE: 9
ccattccaac ttggtctaca a                                                  21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: 3' primer

<400> SEQUENCE: 10
ggaaccattt ctaggacaat g                                                  21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: 5' primer

<400> SEQUENCE: 11
cgaggccgga ttctgggtgg ccag                                               24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: 3' primer

<400> SEQUENCE: 12
tcgatccaca tccggtagga tg                                                 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: 5' primer

<400> SEQUENCE: 13
cggctgcaga cgctcaccaa                                                    20
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: 3' primer

<400> SEQUENCE: 14
cgccaccagt gcatgaggat                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: 5' primer

<400> SEQUENCE: 15
gctgcagaag atagacaaat                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: 3' primer

<400> SEQUENCE: 16
gggatcctca cacagcagtt                                               20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: 5' primer

<400> SEQUENCE: 17
ctgctagcat cgagacctt                                                19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: 3' primer

<400> SEQUENCE: 18
cgagcataga cgaagagcat                                               20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: 5' primer

<400> SEQUENCE: 19
ctcagcagcg agtgactggg ac                                            22

<210> SEQ ID NO 20
<211> LENGTH: 22
<212> TYPE: DNA
<213> ORGANISM: Artificial Sequence
<220> FEATURE:

```
<223> OTHER INFORMATION: Description of Artificial Sequence: 3' primer

<400> SEQUENCE: 20
ccctgagtag gcgccaatga gg                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: 5' primer

<400> SEQUENCE: 21
gtagcctgat catcaacatc cg                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: 3' primer

<400> SEQUENCE: 22
cctgcccatc aaactctgtc ac                                              22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: 5' primer

<400> SEQUENCE: 23
atggcgagcc ctccggatac cg                                              22

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: 3' primer

<400> SEQUENCE: 24
cctctccaac gccagaagct gcc                                             23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: 5' primer

<400> SEQUENCE: 25
ggataatggt gactataccg aga                                             23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: 3' primer

<400> SEQUENCE: 26
ctcacatcga tggcgatata gtt                                             23
```

ANIMAL MODEL

RELATED APPLICATIONS

This application is a continuation-in-part of application Ser. No. 09/085,380, filed May 26, 1998 and now abandoned, and claims benefit of U.S. provisional application No. 60/190,692, filed Mar. 20, 2000, and Swedish application number 9701963-2, filed May 26, 1997.

TECHNICAL FIELD

The invention relates to transgenic non-human mammalian animals being capable of expressing the human FKHL14/FOXC2 gene in its adipose tissue. The invention also relates to methods for identifying compounds useful for the treatment of medical conditions related to obesity or diabetes, said compounds being capable of stimulating expression of the human FKHL14/FOXC2 gene, or being capable of stimulating the biological activity of a polypeptide encoded by the human FKHL14/FOXC2 gene. The invention further relates to methods for identifying compounds useful for the treatment of medical conditions related to malnutrition, said compounds being capable of decreasing expression of the human FKHL14/FOXC2 gene, or being capable of decreasing the biological activity of a polypeptide encoded by the human FKHL14/FOXC2 gene.

BACKGROUND ART

More than half of the men and women in the United States, 30 years of age and older, are now considered overweight, and nearly one-quarter are clinically obese (Wickelgren, 1998). This high prevalence has led to increases in the medical conditions that often accompany obesity, especially non-insulin dependent diabetes mellitus (NIDDM), hypertension, cardiovascular disorders, and certain cancers. Perhaps most importantly, obesity confers a significant increased rate of mortality when compared with that of individuals of normal body weight. Obesity results from a chronic imbalance between energy intake (feeding) and energy expenditure. Energy expenditure has several major components including basal metabolism, physical activity, and adaptive (nonshivering) thermogenesis. This latter process refers to energy that is dissipated in response to changing environmental conditions, most notably exposure to cold or excessive caloric intake (so-called diet-induced thermogenesis). To better understand the mechanisms that lead to obesity and to develop strategies in certain patient populations to control obesity, we need to develop a better underlying knowledge of the molecular events that regulate the differentiation of preadipocytes and stem cells to adipocytes, the major component of adipose tissue.

Role of Adipose Tissue

The reason for existence of the adipocyte is to store energy for use during periods of caloric insufficiency. Postprandially, dietary fat is absorbed via the intestine and secreted into the circulation as large triglyceride (TG) rich particles called chylomicrons (chylo). Lipoprotein lipase (LPL), although produced by adipocytes, is localized to the endothelial cell surface where it hydrolyses TG resulting in the release of free fatty acids (FFA). Much of these are taken up by the adipose tissue either passive or active via FFA transporters. The FFAs are then activated to an acyl CoA form and re-esterfied by an enzymatic cascade to form storage TG. At the same time, glucose, which also increases in the circulation postprandially, is taken up into adipose tissue via specific plasma membrane glucose transporters. These two substrates (glucose and FFA) are the building blocks for formation of storage TG. On the other hand, during fasting, FFAs are released from the adipose tissue TG pool through the action of hormone sensitive lipase (HSL; FIG. 1). Clearly, efficient functioning of adipose tissue is dependent on the coordinated control of each of these processes and the proteins involved.

In recent years, a growing body of evidence has demonstrated a dual role for adipocytes, also being a source of numerous hormones that regulate both the adipocyte itself and many other systems within the body. Adipocytes produce leptin as a function of adipose energy stores. Leptin acts through receptors in the hypothalamus to regulate appetite, activity of brown adipose tissue (BAT), insulin secretion via sympathetic nervous system output, and important neuroendocrine adaptive responses to fasting and control of reproduction. The gene encoding leptin was identified by positional cloning (Zhang et al., 1994) and is the mutation leading to the profound obese phenotype of the ob/ob mouse, characterized by severe obesity, NIDDM, diminished fertility and hypothermia. The db-gene codes for a hypothalamic receptor for leptin (Chua et al., 1996) and the db/db mutant mice show a similar phenotype with ob/ob mice, but here the defect lies in the block of leptin receptor downstream signaling. After leptin administration, it was possible to correct the defect only in the ob/ob, but not db/db mice as predicted by Coleman's parabiosis experiments (Coleman, 1973).

Another adipocyte product, the cytokine tumor necrosis factor α (TNFα), has profound effects on adipocyte differentiation, and energy metabolism, and can even induce adipocyte dedifferentiation and apoptosis. Furthermore, TNFα has more systemic implications as it has been shown to play a role in the genesis of insulin resistance associated with obesity (Hotamisligil et al., 1993). In obese humans and numerous rodent models of obesity-diabetes syndromes, there is a marked elevation in muscle and adipose TNFα production, as compared with tissues from lean individuals (Hotamisligil et al., 1995; Hotamisligil et al., 1993). TNFα levels can be reduced with weight loss (Hotamisligil et al., 1995) or after treatment with the insulin-sensitizing agent pioglitazone (Hofmann et al., 1994).

A third adipocyte product, the acylation stimulating protein (ASP) exert autocrine action on the adipocyte, having potent anabolic effects on human adipose tissue by stimulation of glucose transport and FFA esterification (Maslowska et al., 1997; Walsh et al., 1989). ASP is generated by the interaction of complement D (identical to adipsin), factor B, and complement C3, components of the alternate complement pathway all produced by adipocytes (Choy and Spiegelman, 1996).

White Adipose Tissue Versus Brown Adipose Tissue

There are two different types of adipose tissue in the body, WAT and BAT, which have quite opposite physiological functions although they both have the same "machinery" for lipogenic and lipolytic activity. WAT stores excess energy as triglycerides and releases free fatty acids in response to energy requirements at other sites. BAT on the other hand is involved in adaptive (non-shivering) thermogenesis. BAT is found only at certain sites in the body of rodent, such as in interscapular, perirenal and retroperitoneal regions. In human neonates BAT is present in large quantities but its thermogenic activity decreases shortly after birth and the tissue is gradually converted into white type adipose tissue (Lean et al., 1986). However, judged by expression of the brown fat specific uncoupling protein 1 (UCP1) mRNA, substantial amounts of brown adipocytes exist throughout life in human adipose deposits, which are generally classified as white (Krief et al., 1993).

Brown adipocytes have a multilocular disposition of fat droplets, i.e. a number of individual droplets within each adipocyte, whereas the white adipocyte has a single fat droplet within the cell. Furthermore, the brown adipocyte has a central nucleus and a large number of mitochondria in contrast to the white adipocyte, which has very few mitochondria and a nucleus that is displaced towards the plasma membrane by the lipid droplet. The only known gene marker to distinguish BAT from WAT, or any other cell types is the expression of UCP1 in brown adipocytes. Due to the presence of this unique mitochondrial protein brown adipocytes have the ability of facultative heat production, which is highly regulated by sympathetic nerve activity. UCP1 is a proton translocator in the inner mitochondrial membrane and functions as a facultative uncoupler of the mitochondrial respiratory chain (Nicholls and Locke, 1984). Recently two new uncoupling proteins have been identified and cloned through their sequence homology with UCP1. UCP2 is found in most tissues (Fleury et al., 1997), while UCP3 is expressed in BAT and skeletal muscle (Boss et al., 1997). The respective roles for UCP2 and UCP3 in thermogenesis and energy balance of intact animals remain to be determined. That brown fat is highly important in rodents for maintaining nutritional homeostasis is predicted by the facts that the function of BAT is impaired in obese rodents (Himms-Hagen, 1989) and transgenic mice with decreased brown fat mass develop obesity (Lowell et al., 1993). Since BAT is much less obvious in large animals like humans, than in rodents, skeletal muscle is thought to be the site of primary importance for normally occurring adaptive thermogenesis in large animals.

Both white and brown fat are innervated under the control of the sympathetic nervous system. There are at least three pharmacologically distinct subtypes of β-adrenergic receptors ($\beta_1$, $\beta_2$, and $\beta_3$) found in adipocytes. The $\beta_3$-adrenergic receptor ($\beta_3$-AR) is the predominant subtype in adipose tissue and it mediates the effects of norepinephrine present in the sympathetic synaptic cleft during nerve stimulation of lipolysis in WAT and BAT and of thermogenesis in BAT (Giacobino, 1995). Increased lipolysis takes place primarily through the production of cAMP and the activation of hormone-sensitive lipase through phosphorylation (FIG. 1). Thermogenesis in BAT is accomplished by increased UCP1 mRNA levels through stimulation of transcription (Rehnmark et al., 1990; Ricquier et al., 1986). Uncoupled respiration is also thought to be stimulated by increased lipolysis and the raise in intracellular concentration of FFA (Jezek et al., 1994). Sympathetic stimulation of brown fat also contributes to regulation of energy expenditure by increasing mitochondrial biogenesis (Wu et al., 1999a) and hyperplasia of brown adipocytes. In rodents, $\beta_3$-adrenergic receptors ($\beta_3$-ARs) are abundant in WAT and BAT (Granneman et al., 1991; Muzzin et al., 1991; Nahmias et al., 1991), while in humans, $\beta_3$-AR mRNA is abundant in BAT only, with much less or no $\beta_3$-AR mRNA found in WAT (Granneman and Lahners, 1994; Krief et al., 1993). Long-term treatment of obese rodents with $\beta_3$-selective agonists reduces fat stores and improves obesity-induced insulin resistance (Bloom et al., 1992; Cawthorne et al., 1992; Holloway et al., 1992). Thus, $\beta_3$-selective agonists are promising anti-obesity compounds. Trials of $\beta_3$-AR agonist treatment, aimed at stimulating BAT in humans have proved disappointing with respect to weight loss (Arch and Wilson, 1996). The true potential of $\beta_3$-AR agonists in humans can only be evaluated when a compound with good selectivity and efficacy at the human $\beta_3$-AR, coupled with a long duration of action in vivo, has been identified, however those compounds that have been evaluated in humans so far have much lower efficacy at the human than the rodent receptor. This could be explained by the fact that human and mouse/rat $\beta_3$-AR show a ~80% similarity in their amino acid sequence. Several of the $\beta_3$-AR-selective agonists (e.g. BRL 37344 and CL 316,243) have been shown to be extremely potent against mouse and rat $\beta_3$-AR but with a greatly reduced activity against the human $\beta_3$-AR. Presently, recombinant cell lines expressing human $\beta_3$-ARs are being used to identify compounds with an increased potency against the human receptor (Ito et al., 1998). Mice with targeted mutagenesis of the $\beta_3$-AR gene show only a modest tendency to become obese and their brown fat response to cold exposure works perfectly normal (Susulic et al., 1995). Deficient mice displayed an up-regulation of $\beta_1$-AR mRNA levels in both white and brown fat which most probably is the reason of the mild phenotype. These results implicate that it is possible that $\beta_1$- and $\beta_2$-ARs also play important roles in innervation of adipose tissue. Moreover, other species, including humans, have higher levels of $\beta_1$- and $\beta_2$-ARs, then $\beta_3$-AR, in adipose tissue (Lafontan and Berlan, 1993).

Adipocyte Differentiation

There has been some great progress during the past few years in the understanding of the adipocyte differentiation program. Most of the work leading to this understanding has been carried out using white preadipose cell lines in culture, notably the C3H10T½ and NIH 3T3 fibroblastic cell lines and the 3T3-L1 and 3T3-F442A preadipocyte cell lines. Treatment of multipotent C3H10T½ cells with 5-azacytidine (a demethylating agent) gives rise to cells committed to the myogenic, adipogenic, osteoblastic, or chondrogenic lineages. This is consistent with the view that the adipose lineage arises from the same multipotent stem cell population of mesodermal origin that gives rise to the muscle and cartilage lineages (Cornelius et al., 1994). Under appropriate hormonal control (e.g. glucocorticoid, insulin-like growth factor-1, and cyclic AMP or factors that mimic these agents) or experimental manipulation white preadipose cell lines are capable to differentiate into mature white adipocytes (Ailhaud et al., 1992). Several transcription factors have been identified, which act co-operatively and sequentially to trigger the functional differentiation program (FIG. 2).

Transcriptional Control of Adipocyte Differentiation Through PPARs C/EBPs, and ADD1/SREBP1

Peroxisome proliferator-activated receptors (PPARs) are a class of the nuclear hormone receptors. The member PPARγ is now well recognized as serving an important role in the regulation of adipogenesis. Through the use of alternate promoters, the gene encoding PPARγ gives rise to two separate products, PPARγ1 and PPARγ2, the latter containing an additional 28 N-terminal amino acids that are reported to enhance ligand binding (Fajas et al., 1997; Werman et al., 1997). Reports that ligand activation of retrovirally expressed PPARγ2 in non-differentiating NIH-3T3 cells potently promoted adipocyte differentiation provided the most compelling evidence for the adipogenic nature of PPARγ2 (Tontonoz et al., 1994b). One live-born PPARγ deficient mouse has been produced and it displayed a total absence of WAT and BAT (complete lipodystrophy) and fatty liver, secondary to lipodystrophy (Barak et al., 1999).

Members of the PPAR family specifically function as heterodimers with the retinoid X receptor (RXR) through interactions with peroxisome proliferator response elements (PPREs) on target genes, including lipoprotein lipase (LPL; Schoonjans et al., 1996), the adipocyte fatty acid-binding protein 422/aP2 (Tontonoz et al., 1994a), phosphoenolpyruvate carboxykinase (PEPCK; Tontonoz et al., 1995), and stearocyl-CoA desaturase 1 (Miller and Ntambi, 1996). Transcriptional activity of PPARγ is induced following binding of either synthetic or naturally occurring ligands, including prostaglandins of the D2 and J2 series, with the 15-deoxy-Δ 12, 14-prostaglandin J2 derivate emerging as one of the most potent (Forman et al., 1995). Synthetic ligands that activate PPARγ include carbacyclin and a new class of antidiabetic drugs, the thiazolidinediones (TZDs) (Lehmann et al., 1995). TZDs promote adipogenesis in culture and improve insulin sensitivity in vivo. PPARγ activators probably modify the production of adipocyte-derived mediators of insulin resistance, such as free fatty acids or TNFα. PPARγ activation will decrease production of TNFα by adipocytes and interfere with its inhibitory effect on insulin signaling (Peraldi et al., 1997).

In addition, because of its tissue selective effects on genes involved in fatty acid uptake, PPARγ activation will induce repartitioning of fatty acids in the body, with enhanced accumulation of fatty acids in adipose tissue at the expense of a relative depletion of muscle fatty acids (Martin et al., 1997). The relative lipid depletion of muscle cells will improve their glucose metabolism and result in an improvement in insulin sensitivity. Furthermore, PPARγ decreases the expression of the adipocyte-derived signaling molecule leptin, which results in an increase in energy intake and optimization of energy usage, contributing further to PPARγ's adipogenic effect (De Vos et al., 1996). Recently it has been demonstrated that interaction with a novel cofactor PPARγ coactivator (PGC-1), could enhance PPARγ transcriptional activity in brown adipose tissue (Puigserver et al., 1998).

Three members of the CCAAT/enhancer-binding protein (C/EBP) family of transcription factors, i.e. C/EBPα, C/EBPβ, and C/EBPδ, have been implicated in the induction of adipocyte differentiation. The factors are proteins of the bZIP class, with a basic domain that mediates DNA binding and a leucine zipper dimerization domain. Cyclic AMP and adipogenic hormones such as glucocorticoids and insulin induce a transient increase in the expression of C/EBPβ and δ early in adipocyte differentiation (Cao et al., 1991; MacDougald et al., 1994; Yeh et al., 1995). C/EBPβ, in synergy with C/EBPδ, then induces PPARγ expression in the preadipocyte (Wu et al., 1996, Wu et al., 1995). Mice lacking the C/EBPβ, and C/EBPδ gene have normal expression of C/EBPα and PPARγ, but this co-expression of C/EBPα and PPARγ is not sufficient for complete adipocyte differentiation in the absence of C/EBPβ and C/EBPδ (Tanaka et al., 1997). C/EBPα seems to play an important part in the later stages of differentiation by maintaining the differentiated adipocyte phenotype through autoactivation of its own gene (Lin and Lane, 1992; Lin and Lane, 1994). C/EBPα activates several adipocyte-specific genes such as the insulin-responsive glucose transporter-4 (GLUT4) (Kaestner et al., 1990), 422/aP2 (Christy et al., 1989), UCP1 (Yubero et al., 1994), and also the insulin receptor gene, and insulin receptor substrate 1 (IRS-1) (Wu et al., 1999b). Definitive proof that C/EBPα is required for adipocyte differentiation was obtained by showing that expression of antisense C/EBPα RNA in 3T3-L1 preadipocytes prevented differentiation (Samuelsson et al., 1991). Consistent with this finding, disruption of the C/EBPα gene gave rise to mice that failed to develop white adipose tissue (Wang et al., 1995). Taken together these findings proved that C/EBPα is both required and sufficient to induce adipocyte differentiation. The expression of C/EBPα, as well as other adipocyte genes, is induced upon ligand activation of PPARγ. Through a positive feedback loop, C/EBPα maintains the expression of PPARγ. C/EBPα and PPARγ cooperate to promote adipocyte differentiation, including adipocyte gene expression and insulin sensitivity (Wu et al., 1999b). It is possible that C/EBPα is ultimately an important, indirect target of the antidiabetic actions of the TZDs.

ADD1/SREBP1 (adipocyte determination and differentiation-dependent factor 1/sterol regulatory element binding protein 1) is a member of the basic helix-loop-helix (bHLH) class of transcription factors. In the inactive state, the protein is membrane-bound to the endoplasmic reticulum. Upon activation (such as a low cholesterol state), ADD1/SREBP1 is proteolytically cleaved and the soluble form becomes translocated to the nucleus where it binds one of two different response elements, namely the E box and the sterol regulatory element (SRE; Brown and Goldstein, 1997). The expression of ADD1/SREBP1 is induced during differentiation of adipocytes, where it activates transcription of target genes involved in both cholesterol metabolism and fatty acid metabolism (Kim and Spiegelman, 1996). ADD1/SREBP1 potentiates the transcriptional activity of PPARγ probably through the production of endogenous ligands for PPARγ (Kim et al., 1998) and also by binding to and inducing the PPARγ promoter (Fajas et al., 1999).

When preadipocytes differentiate into adipocytes, several differentiation-linked genes are activated. Lipoprotein lipase (LPL) is one of the first genes induced during this process (FIG. 2). Two cis-regulatory elements important for gradual activation of the LPL gene during adipocyte development in vitro have been delimited (Enerback et al., 1992). These elements, LP-α and LP-β, contained a striking similarity to a consensus sequence known to bind transcription factors of the winged helix family. Results of gel mobility shift assays and DNase I and exonuclease III in vitro protection assays indicated that factors with DNA-binding properties similar to those of the winged helix family of transcription factors are present in adipocytes and interact with LP-α and LP-β. There is a need for identifying human winged helix genes that could be responsible for the induction of the LPL promoter and possibly regulating expression of other adipocyte specific genes.

"Fork Head" and "Winged Helix" Genes

The "fork head" domain is an evolutionary conserved DNA-binding domain of 100 amino acids, which emerged from a sequence comparison of the transcription factor HNF-3α of rat and the homeotic genefork head of Drosophila. X-ray crystallography of the fork head domain from HNF-3γ revealed a three-dimensional structure, the "twinged helix", in which two loops (wings) are connected on the C-terminal side of the helix-turn-helix (Brennan, R. G. (1993) Cell 74, 773–776; Lai, E. et al. (1993) Proc. Natl. Acad. Sci. U.S.A. 90, 10421–10423).

The isolation of the mouse mesenchyme fork head-1 (MFH-1) and the corresponding human (FKHL14) chromosomal genes is disclosed by Miura, N. et al. (1997) Genomics 41, 489–492. The nucleotide sequences of the mouse MFH-1 gene and the human FKHL14 gene have been deposited with the EMBL/GenBank Data Libraries under accession Nos. Y08222 and Y08223 (SEQ ID NO: 1), respectively. The International Patent Application WO 98/54216 (published on Dec. 3, 1998) discloses a gene designated freac11, which encodes a polypeptide identical to polypeptide encoded by the human FKHL14 gene disclosed by Miura.

Figure 1:
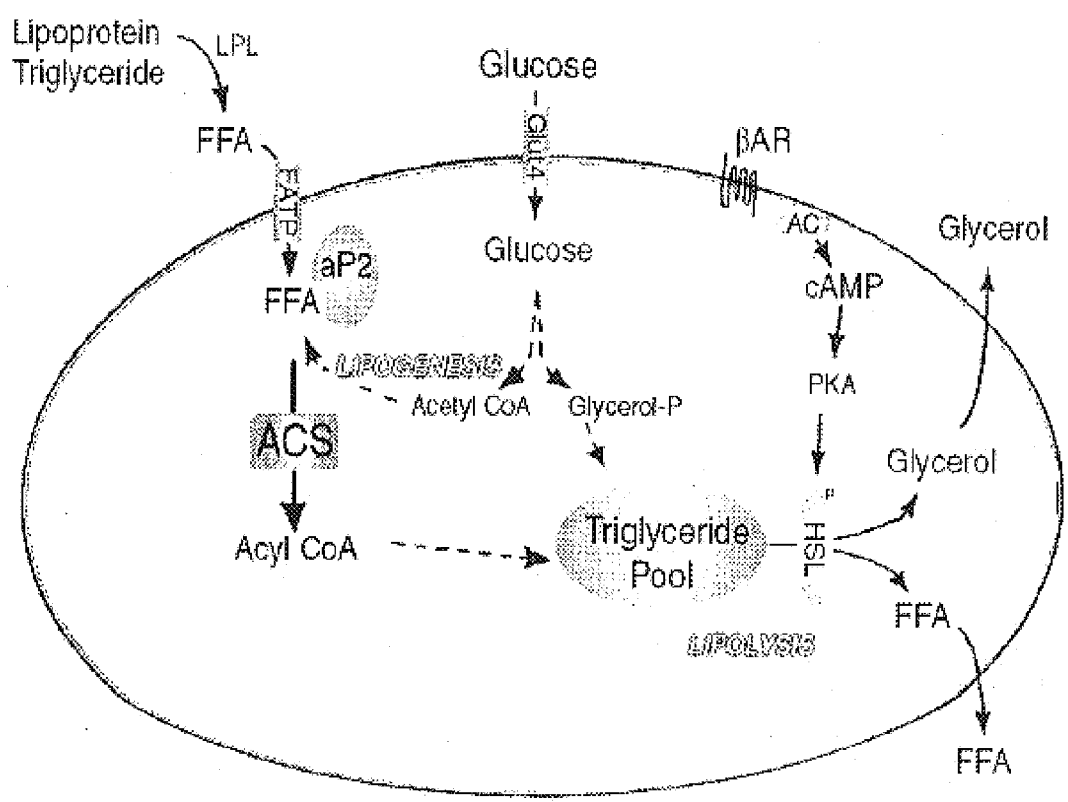
FIG. 1

Schematic view of lipogenic and lipolytic actions in the adipocyte. Triglycerides are hydrolysed to glycerol and free fatty acids by the action of lipoprotein lipase. FFAs are transported into the adipocyte via FATP. FFAs are combined with acetyl CoA to produce acyl CoA, which is re-esterified to triglycerides. The multi-enzyme complex hormone sensitive lipase hydrolyses triglycerides into FFAs and glycerol. FFAs can either be re-esterfied again or be released into the circulation. LPL, lipoprotein lipase; FFA, free fatty acid; FATP, fatty acid transport protein; aP2, adipocyte fatty acid-binding protein 422/aP2; ACS, acyl CoA synthetase; Glut4, glucose transporter IV; βAR, β-adrenergic receptor; AC, adenylate cyclase; PKA, protein kinase A; HSL, hormone sensitive lipase. Figure is adapted from Sethi and Hotamisligil, 1999.

FIG. 2

Summary of different stages and events during in vitro adipocyte differentiation. Our current understanding of adipocyte differentiation indicates that a pluripotent stem cell precursor gives rise to a mesenchymal precursor cell (multipotent) with the potential to differentiate along mesodermal linages of myoblast, chondroblast, osteoblast, and adipocyte. Given appropriate environmental and gene expression cues, preadipocytes undergo clonal expansion and subsequent terminal differentiation. Selected molecular events accompanying this process are indicated above. Pref-1, preadipocyte factor 1; pOb24/A2COL6, α2 chain of type VI collagen; LPL, lipoprotein lipase; aP2, adipocyte fatty acid-binding protein 422/aP2; UCP, uncoupling protein; CUP, C/EBPα undifferentiated protein; FAAR, fatty acid-activated receptor; PPARγ, peroxisome proliferator-activated receptor γ; C/EBP, CCAAT/enhancer binding protein; RXR, retinoid X receptor. Figure is adapted from Klaus, 1997.

FIG. 3

Northern blot analysis of adult human tissues (A) and adult mouse tissues (B). The blots were analyzed with probes specific for FKHL14/FOXC2 (human) and Mfh1 (mouse) respectively. The experiments were carried out with 20 μg of total RNA/lane and β-actin was used as a control.

FIG. 4

CHO cells transient transfected with Ob reporter- and FKHL14/FOXC2 expression plasmids. The Ob promoter activity was determined by a luciferase activity assay. Data are means ±SD from two independent experiments.

FIG. 5

Schematic view of FKHL14/FOXC2 transgene construct and Southern blot detection of integration positive mice. A 2.1-kb fragment containing the FKHL14/FOXC2 cDNA was ligated downstream of the 5.4-kb aP2 enhancer/promoter region (A). Prior to pronuclear injection the transgene construct was liberated from the plasmid as an 8.9-kb NotI/AgeI fragment. A 1.7-kb fragment of the aP2 promoter was used as a probe in Southern blot analysis for identification of integration positive mice. Panel B shows the identification of the three founders investigated further.

FIG. 6

Expression levels of the FKHL14/FOXC2 transgene in white adipose tissue (WAT) and brown adipose tissue (BAT) of wild-type mice (WT) and FKHL14/FOXC2 transgenic mice (founder A, B, and C) as measured by Northern blot analysis (12 μg of total RNA/lane). GAPDH was used as a control.

FIG. 7

A 5-months-old wild-type female and a FKHL14/FOXC2 transgenic female littermate. A, C, and E show WT; B, D, and F show transgenic littermate. (A, B) An exposed dorsal view of the interscapular brown fat pads, illustrating an increased size of the depot in the transgenic mouse. (C, D) An exposed ventral view, illustrating a reduction in size and change in appearance of the intrabdominal white fat pads in the transgenic mouse. (E, F) The interscapular brown fat pads and the intrabdominal white fat pads have been dissected out. BAT at the top and WAT at the bottom.

FIG. 8

Histologic sections of brown fat (A, B), and white fat (C, D) from a 5-months-old wild-type mouse (left) and a FKHL14/FOXC2 transgenic littermate (founder A) (right). (A, B) Interscapular brown fat of the transgenic mouse consists of markedly enlarged adipocytes containing large unilocular fat droplets. (C, D) Adipocytes in white fat of the transgenic mouse show heterogeneity of size. This is in contrast to the WAT from a wild-type mouse, which consists of adipocytes of uniform size filled with a large, unilocular vacuole.

FIG. 9

Change of size of fat depots in FKHL14/FOXC2 transgenic mice (founder C). (A) Weight comparison (expressed as percent of total body weight) for intrabdominal fat depots and interscapular brown fat depots of 5-months-old wild-type females and FKHL14/FOXC2 transgenic littermates. Changes are significant, P<0.005. (B) Ratio between weights of the intrabdominal fat depot and the interscapular brown fat depot. Change is significant, P<0.0005. (C) No significant difference in body weight could be detected between the two groups. (D) No significant difference in food consumption was noticed when measured during a time period of two months. Data are means ±SD, n=3 for both WT and founder C in A-C, n=4 for both WT and founder C in D.

FIG. 10

Amount of different mRNAs in white adipose tissue (WAT) and brown adipose tissue (BAT) of wild-type mice (WT) and FKHL14/FOXC2 transgenic mice (founder A, B, and C) as measured by Northern blot analysis (12 μg of total RNA/lane). GAPDH was used as a control for ensuring equal loading on all blots.

FIG. 11

Serum triglyceride is lowered in FKHL14/FOXC2 transgenic mice (founder A). Serum triglyceride content was analyzed for 14-weeks-old wild-type males and FKHL14/FOXC2 transgenic littermates fed ad libitum. Change is significant, P<0.005. Data are means ±SD, n=4 for both WT and founder A.

FIG. 12

Total body lipid content is lowered in FKHL14/FOXC2 transgenic mice (founder A). Total body lipid content was analyzed for 6-months-old wild-type males and FKHL14/FOXC2 transgenic littermates fed ad libitum. Change is significant, P<0.0005. Data are means ±SD; WT, n=3 and founder A, n=4.

FIG. 13

Blood glucose is lowered (A) and glucose elimination is more efficient (B) in FKHL14/FOXC2 transgenic mice (founder A). (A) Blood glucose levels were analysed for 10-weeks-old wild-type mice and FKHL14/FOXC2 transgenic littermates fed ad libitum. A significant (P<0.05) reduction of blood glucose levels were seen for FKHL14/

FOXC2 transgenic mice. (B) An intravenous glucose tolerance test was carried out on the mice used in (A). Blood samples were taken immediately before and at 1, 5, 20, and 50 min after intravenous injection of glucose (1 g/kg). The values were significantly changed at 0 min (P<0.05), 20 min (P<0.001), and at 50 min (P<0.05). Data are means ±SD; n=10 for both WT and founder A.

FIG. 14

Plasma insulin is lowered in FKHL14/FOXC2 transgenic mice (A), still levels raised higher than in wild-type after intravenous (iv) glucose load (B, C) (founder A). (A) Plasma insulin levels were analyzed for 10-weeks-old wild-type mice and FKHL14/FOXC2 transgenic littermates fed ad libitum. A significant (P<0.05) reduction of plasma insulin levels was seen for FKHL14/FOXC2 transgenic mice. (B) An intravenous glucose tolerance test was carried out on the mice used in (A) Blood samples were taken immediately before and at 1, 5, 20, and 50 min after intravenous injection of glucose (1 g/kg). The values were significantly changed at 0 min (P<0.05), 20 min (P<0.01), and at 50 min (P<0.05). (C) Fold induction of plasma insulin levels one minute after i.v. glucose load. Change is significant, P<0.005. Data are means ±SD; n=10 for both WT and founder A.

FIG. 15

Hypothetical action of FKHL14/FOXC2 in adipocytes. Filled arrow indicates known positive transcriptional regulation. Open arrow represents a proposed action of FKHL14. ADD1/SREBP1 both activates transcription of acetyl CoA carboxylase (Lopez et al., 1996), fatty acid synthase (FAS), and lipoprotein lipase (LPL), and increases the transcriptional activity of PPARγ (Fajas et al., 1999). PPARγ activates transcription of fatty acid transport protein (FATP), acyl-CoA synthetase genes (ACS; Martin et al., 1997), adipocyte fatty acid-binding protein 422/aP2 (aP2; Tontonoz et al., 1994a), LPL (Schoonjans et al., 1996), and phosphoenolpyruvate carboxykinase (PEPCK; Tontonoz et al., 1995). C/EBPα activates insulin-responsive glucose transporter-4 (GLUT4; Kaestner et al., 1990), aP2 (Christy et al., 1989), uncoupling protein 1 (UCP1; Yubero et al., 1994), the insulin receptor (InsR), insulin receptor substrate-1 (IRS-1; Wu et al., 1999b), and PEPCK (Park et al., 1990). A positive feedback loop between C/EBPα and PPARγ have been suggested (Wu et al., 1999b).

FIG. 16

Reduction in weight gain in (transgenic) tg mice. Analysis were performed on tg-A mice with wt littermates as controls, fed ad libitum, mice were approximately 4–6 months of age. There is a reduction in diet induced weight gains in FKHL14/FOXC2tg mice, both in females (p<0.02; a) and males (p<0.03; b), as compared with wt mice, values are means ±SEM, n=4 in each group. Mice were on a high fat diet (58.0% on a caloric basis) for seven weeks (see Methods).

DISCLOSURE OF THE INVENTION

According to the present invention, the human transcription factor gene FKHL14/FOXC2 is identified as a key regulator of adipocyte metabolism. Increased FKHL14/FOXC2 expression, in white (WAT) and brown adipose tissue (BAT), has a pleiotropic effect on gene expression, which leads to resistance to diet induced weight gain and a decrease in: total body lipid content, serum triglycerides, plasma levels of free fatty acids, glucose and insulin. To our knowledge, FKHL14/FOXC2 is the hitherto only identified gene that, in a concerted action, can counteract most, if not all, of the symptoms associated with obesity, including hypertriglyceridemia and insulin resistance—a likely consequence hereof would be protection against type 2 diabetes.

During adulthood, the human winged helix gene FKHL14/FOXC2 is expressed exclusively in adipose tissue. The LPL mRNA levels in the FKHL14/FOXC2 transgenic mice seem to be slightly elevated (FIG. 10), which is in concordance with the initial findings that the two winged helix cis-regulatory elements are responsible for the inducibility of the LPL promoter (Enerback et al., 1992). The higher expression level of LPL most probably is responsible for the significantly decreased plasma TG levels noticed in FKHL14/FOXC2 transgenic mice (FIG. 11), in addition to the fact that the profound up-regulation of adipsin in both WAT and BAT (FIG. 10) most certainly is of great importance. Adipsin is a secreted protein necessary for the formation of acylation stimulating protein (ASP), which has potent anabolic effects on human adipose tissue for both glucose and free fatty acid (FFA) storage (Cianflone et al., 1995).

The extensive alternations seen in the FKHL14/FOXC2 transgenic mice presented here predicts a very central and important role for this winged helix gene hitherto unknown to participate in molecular events in adipose tissue. It has been demonstrated by gene targeting experiments that the mouse homologue, Mfh1, plays a crucial role during embryonic development (Iida et al., 1997; Winnier et al., 1997), but so far nothing has been published about its function in adult mice. In a recent publication an Mfh1/Pax1 double mutant was shown to be totally absent of BAT at day 15.5 dpc (Furumoto et al., 1999).

The FKHL14/FOXC2 transgenic mice had a clear reduction in white adipose tissue mass. The reduced size of the white fat depots might be due solely to the reduction in size of the adipocytes (FIG. 8), but one cannot rule out the possibility that there is also a reduction in adipocyte number. There are a number of possible reasons why the FKHL14/FOXC2 transgenic mice have decreased size of white adipocytes. One might presume an increased lipolytic activity of their adipocytes in general; coupled with the greater mass of brown fat this may lead to increased energy expenditure through heat production by BAT giving rise to the lean phenotype. The upregulation of $\beta_3$-AR seen in transgenic WAT (FIG. 10) will result in an elevated activation of HSL hence an increase in lipolysis (FIG. 1) ultimately leading to reduced lipid storing.

Figure 10:
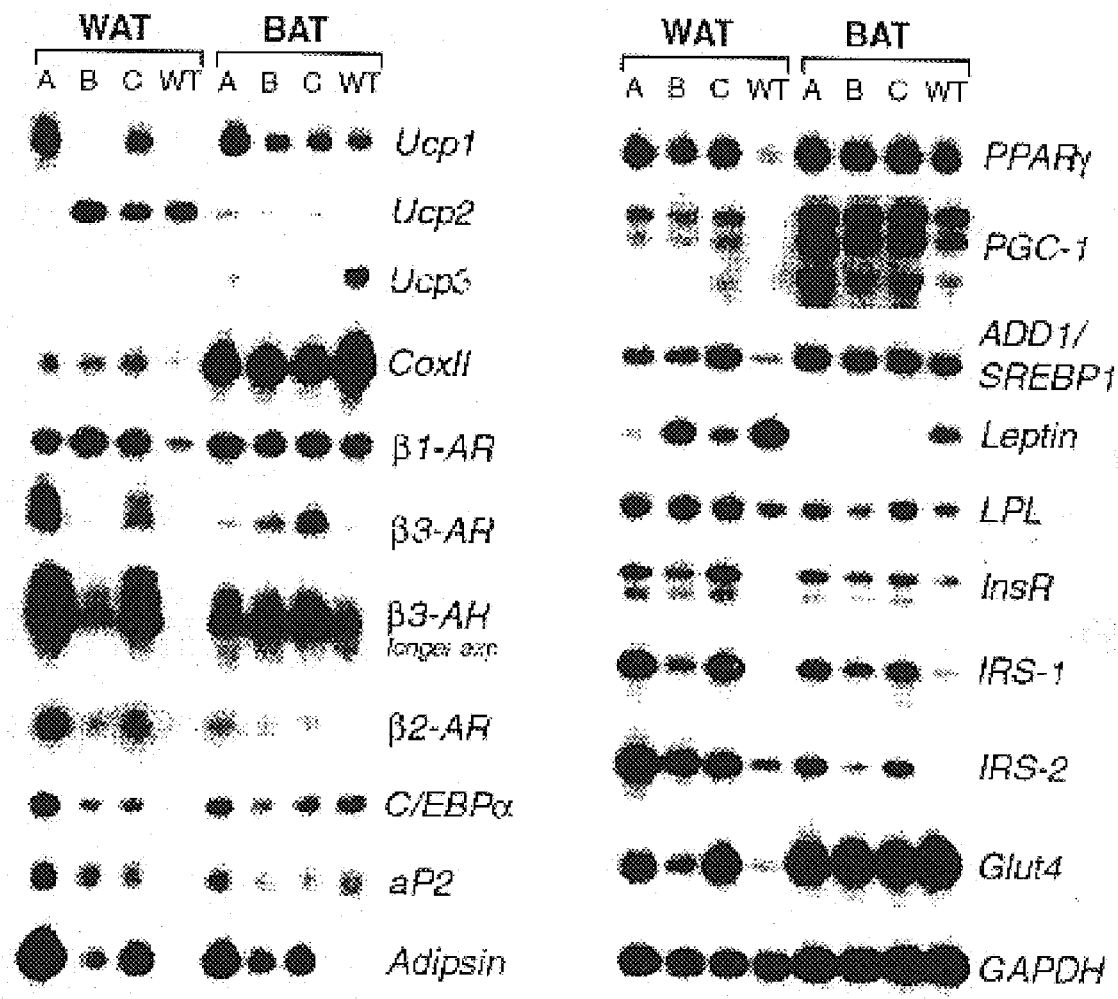
Figure 12:
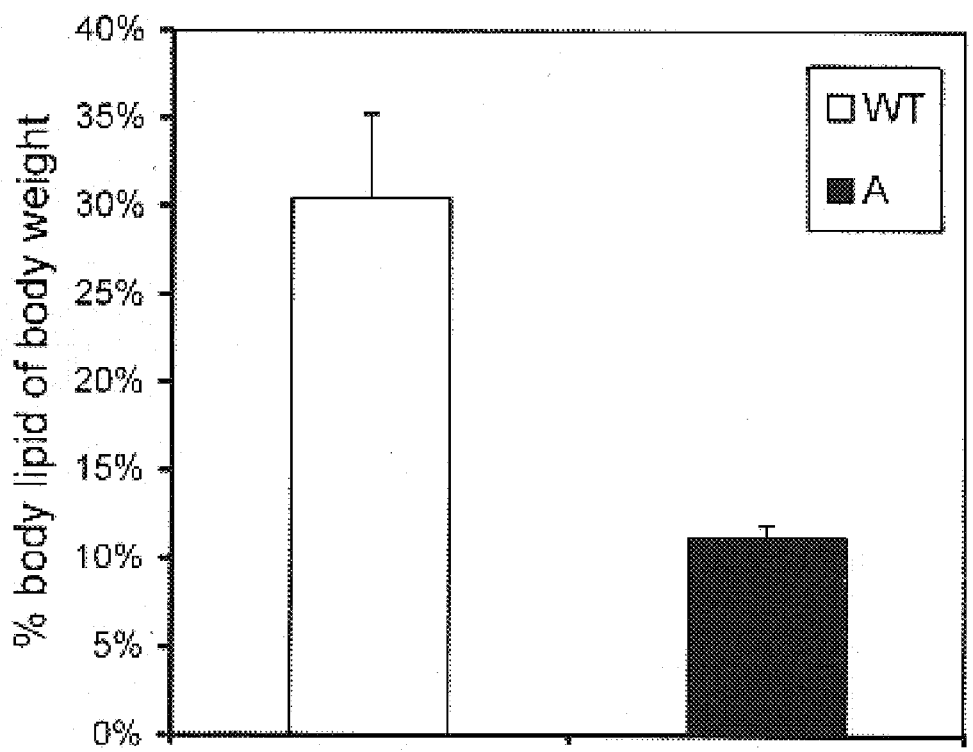

Furthermore, the transgenic mice were insulin sensitive (FIG. 14); this could be explained by both the upregulation of genes involved in insulin action (InsR, IRS-1, IRS-2, and GLUT4; FIG. 10) and the lean body composition (FIG. 12). Insulin has a critical role in lipid metabolism, promoting the storage of triglycerides in adipocytes through numerous actions on this cell. Among these are stimulation of glucose uptake and inhibition of lipolysis, which occur very rapidly through insulin-responsive glucose transporter protein (GLUT 4) translocation or covalent modification of HSL, respectively. Insulin also stimulates fatty acid and triglyceride synthesis, through the induction of key lipogenic enzymes and induction of lipoprotein lipase. The data presented here are compatible with an increased energy turnover in the adipocytes derived from FKHL14/FOXC2 transgenic mice.

Figure 15:
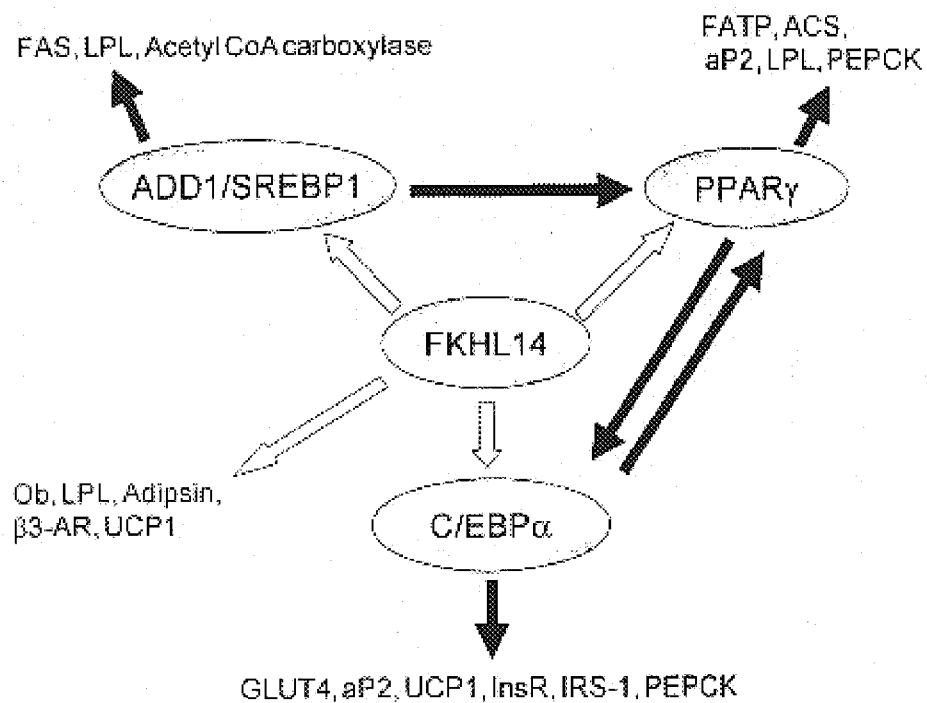

The white fat depots of FKHL14/FOXC2 transgenic mice had an ectopic expression of the brown fat specific marker UCP1 (FIG. 10). The origin of multilocular adipocytes in transgenic WAT (FIG. 8d) remains an enigma. It has been suggested that there is a pool of intraconveritble cells or small brown preadipocytes present in WAT. Studies on both rat and mice have demonstrated atypical occurrence of UCP1 in certain WAT depots previously thought to contain only white adipocytes (Cousin et al., 1992; Loncar, 1991). If submitted to cold or to treatment with a $\beta_3$-AR selective agonist, UCP1 expression was increased in WAT as in typical BAT and on histological sections one could identify small multilocular cells interspersed between the white adipocytes, which were shown to contain UCP1 by immunohistochemistry (Cousin et al., 1992; Ghorbani et al., 1997). Furthermore, both UCP1 and $\beta_3$-AR mRNAs have been detected in white fat depots of human beings (Krief et al., 1993) and recently, it has been shown that cultures of human adipocytes derived from white fat depots express UCP1 after treatment with $\beta_3$-AR agonists (Champigny and Ricquier, 1996). Moreover, transgenic mice overexpressing $\beta_1$-AR in WAT and BAT have abundant appearance of brown fat cells in subcutaneous WAT (Soloveva et al., 1997). We would like to speculate that these suggested intraconveritble cells or small brown preadipocytes have undergone proliferation in our transgenic mice, readily detectable on histological sections as small multilocular cells (FIG. 8d), due to the increased expression of $\beta_3$-AR. The FKHL14/FOXC2 transgene possibly activates other proteins further down the signal transduction pathway finally leading to the induction of UCP1 expression. In addition, the levels of C/EBP$\alpha$ and PPAR$\gamma$ mRNAs in transgenic WAT reaches the ones in wild-type BAT (FIG. 10) and both of these transcription factors are known to induce UCP1 expression (Digby et al., 1998; Yubero et al., 1994). C/EBP$\alpha$ activates several adipocyte-specific genes and also genes involved in insulin action (FIG. 15), hence C/EBP$\alpha$ (−/−) cells show a complete absence of insulin-stimulated glucose transport, secondary to reduced gene expression and tyrosine phosphorylation for the insulin receptor and IRS-1 (Wu et al., 1999b). The WAT of FKHL14/FOXC2 transgenic mice have marked elevation of the mRNA levels for both C/EBP$\alpha$ and PPAR$\gamma$, these transcription factors may in turn be responsible for upregulation of mRNA levels for aP2, LPL, UCP1, GLUT4, insulin receptor, and IRS-1 (FIG. 15)

It is interesting to note that the white adipocytes of FKHL14/FOXC2 transgenic mice have not just converted into brown adipocytes, in the meaning of mRNA expression, as they have for example higher levels of certain mRNAs (i.e. $\beta_2$-AR, insulin receptor, IRS-1, and IRS-2) than seen in any type of wild-type adipose tissue.

Figure 2:
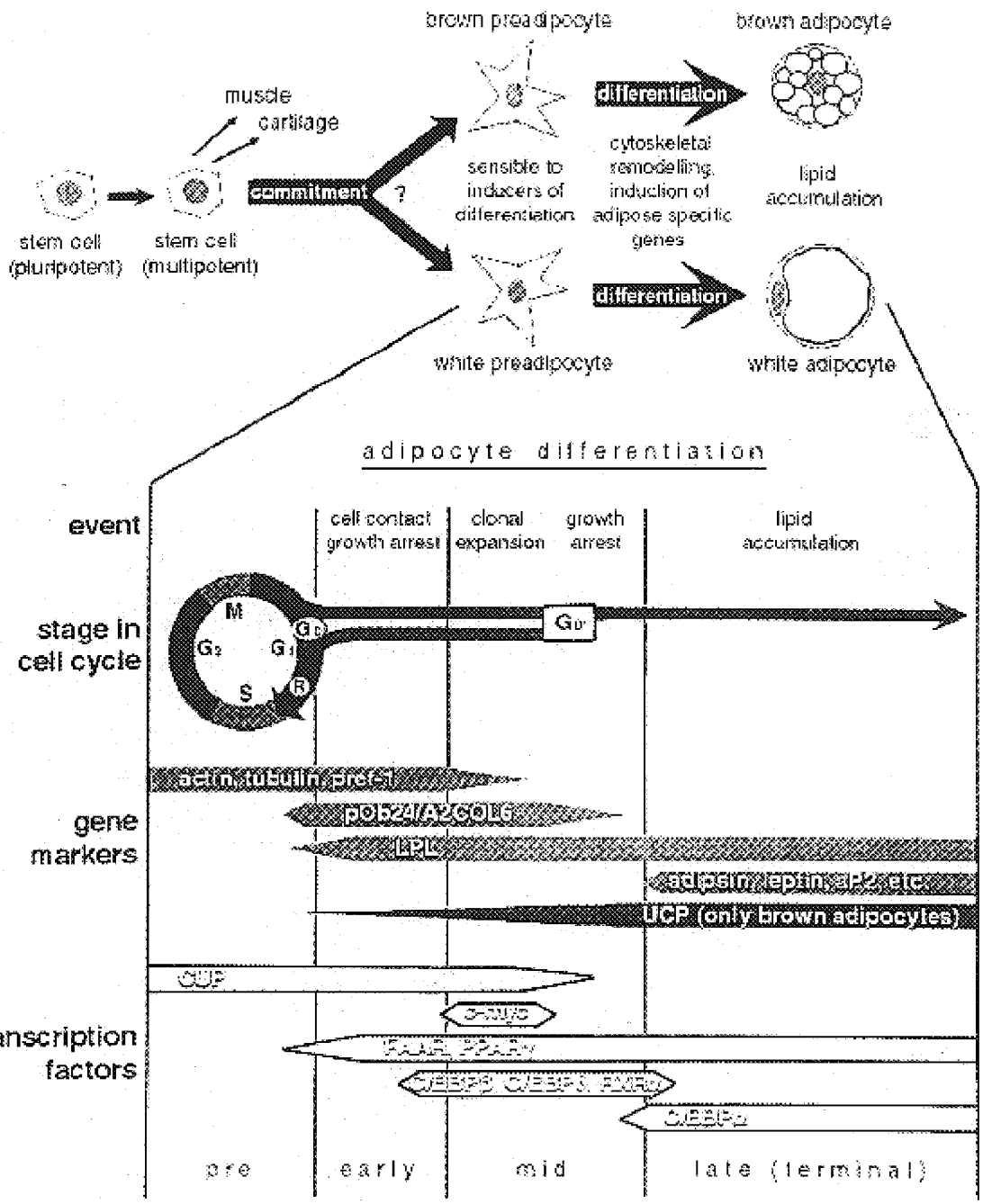

In the mice studied here, FKHL14/FOXC2 transgene expression was under the control of the aP2 promoter, which only functions in adipocytes and not in stem cells and probably neither in intraconveritble cells discussed above (Ailhaud et al., 1992). Considering the fact that aP2 is a late marker (FIG. 2) it is quite surprising that we obtain such a dramatic change in the characteristics of white adipocytes. Currently, it is not known if adipocyte dedifferentiation occurs in vivo, whereas it has been demonstrated in vitro that this process occurs and is induced by TNF$\alpha$ in human adipocytes (Petruschke and Hauner, 1993). Another interpretation for the occurrence of small multilocular cells in WAT of our transgenic mice could then be a dedifferentiation of originally white adipocytes followed by a conversion into the type of adipocytes observed in the FKHL14/FOXC2 transgenic mice.

The interscapular brown fat of FKHL14/FOXC2 transgenic mice weighed ~7.5 times as much as wild-type brown fat (FIG. 9a). This extreme hypertrophy might be explained by the increased expression of $\beta_3$- and $\beta_2$-AR mRNA seen in BAT of FKHL14/FOXC2 transgenic mice (FIG. 10).

Figure 8A:
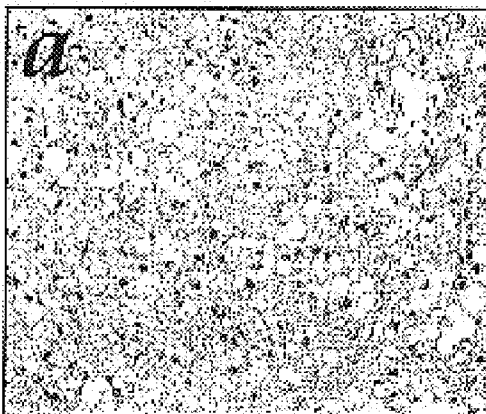
Figure 8B:
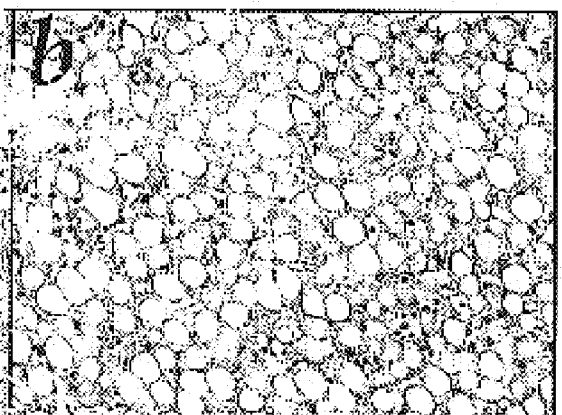

Chronic treatment with $\beta_3$-AR agonists increases body temperature and energy expenditure and it causes hypertrophy of the interscapular BAT, with several fold increases in the content of UCP1 and cytochrome oxidase (Himms-Hagen et al., 1994). The morphology of transgenic interscapular BAT is somewhat changed having larger fat droplets than wild-type BAT (FIGS. 8a & b). This is not a feature of chronic $\beta_3$-AR agonist treatment, but there is a possibility that the upregulation of markers involved in insulin action (FIG. 10) and elevated levels of adipsin promotes the increased storage of triglycerides in brown adipocytes of transgenic mice. It has also been noticed before that elevated levels of UCP2 mRNA can be coupled to this phenotype (Enerback et al., 1997; Kozak et al., 1991).

Dysfunctional BAT seen in the ADD1/nSREBP-1c transgene (Shimomura et al., 1998) and genetically ablated BAT in the UCP1-DTA transgene (UCP1 promoter—diphtheria toxin A chain) (Lowell et al., 1993) leads to insulin resistance. Transgenic mice overexpressing ADD1/nSREBP-1c displays several features quiet opposite the ones of the FKHL14/FOXC2 transgene, including insulin resistance and NIDDM. FKHL14/FOXC2 transgenic mice displays a somewhat opposite change of expression pattern compared with that of ADD1/nSREBP-1c transgenic mice, there the mRNAs encoding PPAR$\gamma$, C/EBP$\alpha$, aP2, UCP1, adipsin, InsR, IRS-1, IRS-2, and GLUT4 all are downregulated. In our transgene all of this mRNAs are instead upregulated (FIG. 10). However, intriguingly our transgenic mice actually have raised levels of ADD1/SREBP1 mRNA in WAT (FIG. 10) somewhat mimicking the ADD1/nSREBP-1c transgene in that regard.

Figure 4:
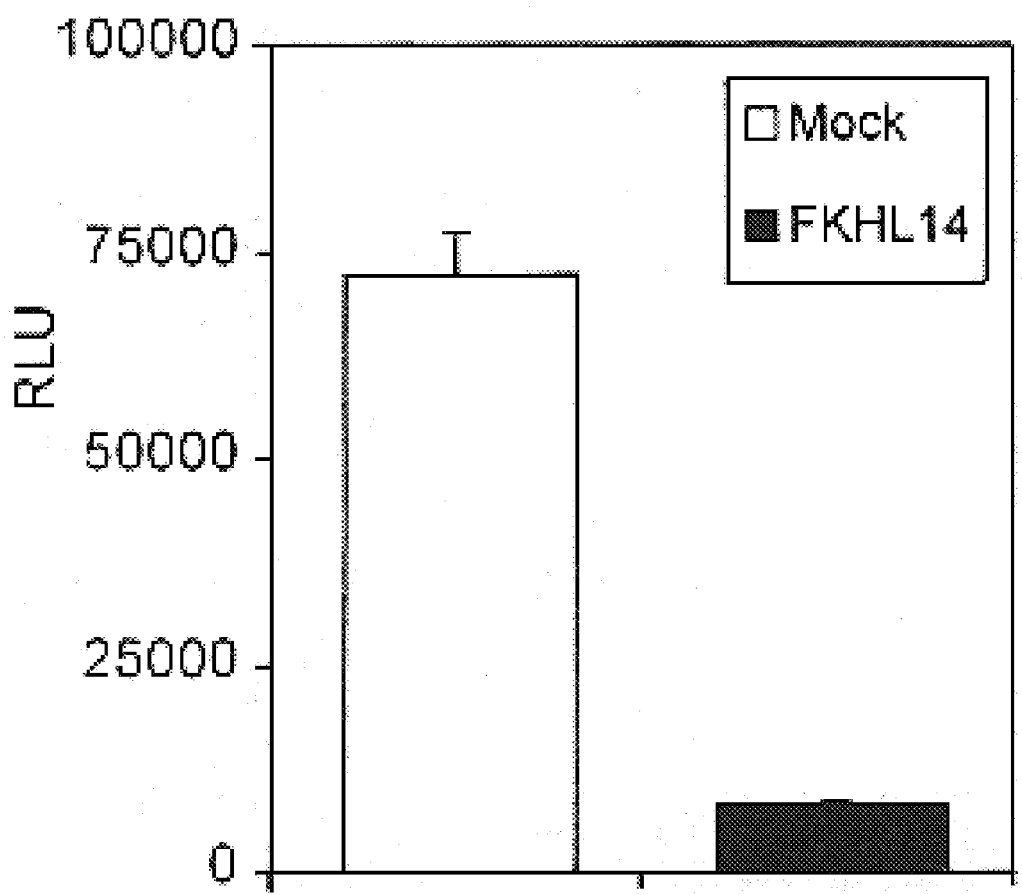

FKHL14/FOXC2 might be an important participant in the regulation of leptin expression, based on the fact that leptin mRNA levels are down-regulated in FKHL14/FOXC2 transgenic mice (most prominent in BAT; FIG. 10), and the ten-fold decrease of Ob promoter activity seen in cell culture experiments then cotransfected with FKHL14/FOXC2 expression plasmid (FIG. 4). In addition, leptin expression is inhibited by $\beta_3$-adrenergic stimuli (Mantzoros et al., 1996), which is presumed to be high in FKHL14/FOXC2 transgenic mice due to the up-regulation of $\beta_3$-AR mRNA levels.

The amount of food consumed by transgenic mice compared to that of wild-type did not differ (FIG. 9d), and no significant difference in body weight has been observed, predicting that the difference observed in total body lipid content must be compensated with an increased anabolism in FKHL14/FOXC2 transgenic mice. The FKHL14/FOXC2 transgenic mice most probably also are protected against developing diet-induced obesity, taking in consideration the observed insulin sensitivity (FIG. 14), the lower blood glucose levels and more efficient glucose elimination (FIG. 13) observed in our transgenic mice. Insulin sensitivity and/or resistance to diet-induced obesity have been observed for several other transgenic mouse models: targeted disruption of the RII$\beta$ subunit of protein kinase A results in lean mice resistant to diet-induced obesity (Cummings et al., 1996), mice lacking the protein tyrosine phosphatase-1B gene (PTP-1B) are insulin sensitive and resistant to obesity (Elchebly et al., 1999), aP2-UCP1 transgenic mice are prevented against genetic obesity (Kopecky et al., 1995), and transgenic mice overexpressing the $\beta_1$-AR in adipose tissue are resistant to obesity (Soloveva et al., 1997). Moreover, $\beta_3$-AR agonists have been found to have antidiabetic effects in animal models of obesity and NIDDM; chronic dosing can improve glucose tolerance, increase insulin sensitivity and reduce fasting blood glucose levels (Cawthorne et al., 1992). FKHL14/FOXC2 is the only adipocyte specific gene that, directly or indirectly, regulates triglyceride metabolism, adrenergic regulation and insulin action in adipocytes. Actually, the FKHL14, is to our knowledge the only known gene that, in a concerted action, can counteract most, if not all, of the symptoms associated with obesity: hypertriglyceridemia, insulin resistance and most likely the associated clinical syndrome of NIDDM.

The apparent FKHL14/FOXC2 transgene dose responsive effect observed in WAT for the induction of UCP1, $\beta_3$-AR, and adipsin, may indicate a direct interaction for FKHL14/FOXC2 with the promoters of these genes. A schematic view of the hypothetical action of FKHL14/FOXC2 in adipocytes is shown in FIG. 15.

According to the present invention, proper activation of FKHL14/FOXC2 by drugs may decrease fat stores, while preserving skeletal muscle mass, by preventing fat assimilation during digestion and by increasing WAT lipolysis, BAT thermogenesis, and insulin action. Such drugs may thus prove useful in treating obesity and NIDDM as well as associated diseases. It is thus foreseen that an effective amount of a polypeptide encoded by the human FKHL14/FOXC2 gene, could be useful in methods for the treatment of medical conditions related to obesity.

In another aspect, this invention relates to a construct, or more specifically a gene construct or recombinant construct, comprising a human FKHL14/FOXC2 nucleotide sequence operably linked to an element selected from the group consisting of promoters, response elements, enhancer elements and mixtures thereof. The term "operably linked" as used herein means functionally fusing an element with a structural gene in the proper frame to express the structural gene under control of the element.

Figure 5A:
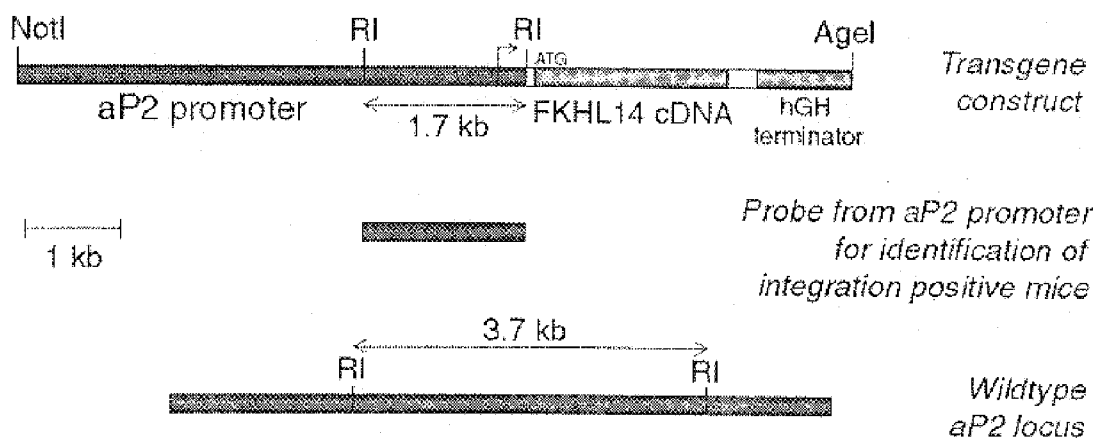

Preferably, the said element is a promoter, in particular an adipose-specific promoter such as the adipose-specific promoter of the murine gene encoding adipocyte P2 (FIG. 5), which can be isolated as described by Ross et al. (1990).

In a preferred form of the invention, the said FKHL14/FOXC2 nucleotide sequence is identical or substantially similar with SEQ ID NO: 1 of the Sequence Listing. However, the FKHL14/FOXC2 nucleotide sequence is not to be limited strictly to the sequence shown as SEQ ID NO: 1. Rather the invention encompasses constructs comprising nucleotide sequences carrying modifications like substitutions, small deletions, insertions or inversions, which nevertheless encode polypeptides having substantially the biochemical activity of the FKHL14/FOXC2 polypeptide.

Consequently, included in the invention are constructs wherein the said human FKHL14/FOXC2 nucleotide sequence is selected from:

(a) the nucleotide sequence shown as SEQ ID NO: 1;

(b) nucleotide sequences capable of hybridizing, under stringent hybridization conditions, to a nucleotide sequence complementary to the polypeptide coding region of a nucleotide sequence as defined in (a) and which codes for a biologically active FKHL14/FOXC2 polypeptide, or a functionally equivalent modified form thereof;

(c) nucleic acid sequence which are degenerate as a result of the genetic code to a nucleotide sequence as defined in (a) or (b) and which codes for a biologically active FKHL14/FOXC2 polypeptide, or a functionally equivalent modified form thereof; and (d) nucleotide sequences which are at least 90% homologous, preferably at least 95% homologous, with the nucleotide sequence shown as SEQ ID NO: 1 in the Sequence Listing.

The term "stringent hybridization conditions" is known in the art from standard protocols (e.g. Ausubel et al) and could be understood as e.g. hybridization to filter-bound DNA in 0.5 M NaHPO$_4$, 7% sodium dodecyl sulfate (SDS), 1 mM EDTA at +65° C., and washing in 0.1×SSC/0.1% SDS at +68° C.

In another aspect, the invention provides a transgenic non-human mammalian animal whose genome comprises a gene construct as defined above, said animal being capable of expressing the human FKHL14/FOXC2 gene in its adipose tissue. By "transgenic animal" is meant a non-human mammalian animal that includes a nucleic acid sequence which is inserted into a cell and becomes a part of the genome of the animal that develops from that cell. Such a transgene may be partly or entirely heterologous to the transgenic animal. Although transgenic mice represent a preferred embodiment of the invention, other transgenic mammals, including transgenic rodents (for example, hamsters, guinea pigs, rabbits, and rats), and transgenic pigs, cattle, sheep, and goats may be constructed by standard techniques and are included in the invention.

One means available for producing a transgenic animal, with a mouse as an example, is as follows: Female mice are mated, and the resulting fertilized eggs are dissected out of their oviducts. The eggs are stored in an appropriate medium. DNA or cDNA encoding the FKHL14/FOXC2 gene is purified from a vector by methods well known in the art. Tissue specific regulatory elements, such as the adipocyte-specific aP2 promoter discussed above, may be fused with the coding region to permit tissue-specific expression of the trans-gene. The DNA, in an appropriately buffered solution, is put into a microinjection needle and the egg to be injected is put in a depression slide. The needle is inserted into the pronucleus of the egg, and the DNA solution is injected. The injected egg is then transferred into the oviduct of a pseudopregnant mouse, where it proceeds to the uterus, implants, and develops to term.

A transgenic mouse according to the invention could preferably be derived from a genetically obese mouse. Genetically obese mice, such as ob/ob or db/db mice, are well known in the art.

In a further aspect, the invention provides an isolated cell line derived from the transgenic non-human mammalian animal. In yet another aspect, the invention provides a method for producing a transgenic non-human mammalian animal overexpressing the human FKHL14/FOXC2 gene, said method comprising chromosomally incorporating a gene construct comprising the human FKHL14/FOXC2 gene, together with suitable regulatory sequences, into the genome of said non-human mammalian animal.

The invention also provides a method for studying the biological activity of a polypeptide encoded by the human FKHL14/FOXC2 gene, said method comprising the steps (i) producing a transgenic non-human mammalian animal overexpressing the human FKHL14/FOXC2 gene; and (ii) comparing the phenotype of the said transgenic non-human mammalian animal with a wild-type animal of the same species.

In further important aspects, the invention provides biological screening assays for the identification of compounds that could be useful for the treatment of medical conditions related to obesity, or alternatively, to malnutrition. A "medical condition related to obesity" includes e.g. obesity, NIDDM, hypertension and hyperlipidemia. The said "medical condition related to malnutrition" includes e.g. anorexia, ineffective metabolism, and cancer.

Consequently, the invention provides a method for identifying a compound useful for the treatment of a medical condition related to obesity, said method comprising the steps (i) contacting a test compound with the human FKHL14/FOXC2 gene; and (ii) determining whether said test compound activates the expression of the human FKHL14/FOXC2 gene, such activation being indicative for a compound useful for the treatment of a medical condition related to obesity.

In another aspect, the invention provides a method of screening for a compound useful for the treatment of a medical condition related to obesity, said method comprising exposing a non-human mammalian animal to a test compound, and determining the activity of said human FKHL14/FOXC2 gene in said non-human mammalian animal, wherein an increase in said gene activity as compared to an untreated non-human mammalian animal being indicative of a compound useful for the treatment of a medical condition related to obesity.

The said non-human mammalian animal is preferably a mouse, for example an obese mouse. Mice can be rendered obese by administration of a high-fat diet. Alternatively, the mouse can be a genetically obese mouse, such as an ob/ob or db/db mouse.

In the methods described above, the activity of the human FKHL14/FOXC2 gene in said non-human mammalian animal, can advantageously be compared to the activity of the said human FKHL14/FOXC2 gene in a transgenic non-human mammalian animal expressing or overexpressing the said human FKHL14/FOXC2 gene.

In an alternative method for identifying a compound useful for the treatment of a medical condition related to obesity, the method comprises the steps (i) contacting a test compound with a polypeptide encoded by the human FKHL14/FOXC2 gene; and (ii) determining whether said test compound stimulates the biological activities of the said polypeptide, such stimulation being indicative for a compound useful for the treatment of a medical condition related to obesity. The term "biological activities", as used in this context, means e.g. enhancing the DNA-protein interaction between the FKHL14/FOXC2 polypeptide and target sequences in promoters of target genes.

The invention further provides a method for identifying a compound useful for the treatment of a medical condition related to malnutrition, said method comprising the steps (i) contacting a test compound with the human FKHL14/FOXC2 gene; and (ii) determining whether said test compound decreases or inhibits expression of the FKHL14/FOXC2 gene, such decrease or inhibition being indicative for a compound useful for the treatment of a medical condition related to malnutrition.

Also included in the invention is a method of screening for a compound useful for the treatment of a medical condition related to malnutrition, said method comprising exposing a non-human mammalian animal, preferably a mouse, such as an obese mouse, to a test compound, and determining the activity of said human FKHL14/FOXC2 gene in said non-human mammalian animal, wherein a decrease in said gene activity as compared to an untreated non-human mammalian animal being indicative of a compound useful for the treatment of a medical condition related to malnutrition.

In an alternative method for identifying a compound useful for the treatment of a medical condition related to malnutrition, the method comprises the steps (i) contacting a test compound with a polypeptide encoded by the human FKHL14/FOXC2 gene; and (ii) determining whether said test compound decreases or inhibits the biological activities of the said polypeptide, such decrease or inhibition being indicative for a compound useful for the treatment of a medical condition related to malnutrition.

For therapeutic uses, the compositions or agents identified using the methods disclosed herein may be administered systemically, for example, formulated in a pharmaceutically acceptable buffer such as physiological saline. Preferable routes of administration include, for example, oral, subcutaneous, intravenous, intraperitoneally, intramuscular, or intradermal injections, which provide continuous, sustained levels of the drug in the patient. Treatment of human patients or other animals will be carried out using a therapeutically effective amount of an identified compound in a physiologically acceptable carrier. Suitable carriers and their formulation are described, for example, in Remington's Pharmaceutical Sciences by E. W. Martin. The amount of the active compound to be administered varies depending upon the manner of administration, the age and body weight of the patient, and with the type of disease and extensiveness of the disease. Generally, amounts will be in the range of those used for other agents used in the treatment of obesity and diabetes.

In a further important aspect of the invention, the human FKHL14/FOXC2 gene could be used in gene therapy of medical conditions related to obesity. Included in the invention is thus a method of treating obesity in a human, comprising (i) administering to the said human a vector comprising a human FKHL14/FOXC2 DNA sequence operably linked to a promoter; and (ii) allowing the said human to express a therapeutically effective amount of a polypeptide encoded by said human FKHL14/FOXC2 gene. A gene delivery system including said vector, comprising a human FKHL14/FOXC2 DNA sequence operably linked to a promoter, is in itself another aspect of the invention.

The FKHL14/FOXC2 gene should be operably linked to at least one element which allows for expression of the gene when introduced into the host cell environment. These sequences include promoters, response elements, and enhancer elements. Preferred is the adipose-specific promoter/enhancer of the murine gene encoding adipocyte P2

The heterologous gene may be delivered to the organism using a vector or other delivery vehicle. DNA delivery vehicles can include viral vectors such as adenoviruses, adeno-associated viruses, and retroviral vectors. See, for example: Chu et al. (1994) Gene Ther 1: 292–299; Couture et al. (1994) Hum Gene Ther 5:667–677; and Eiverhand et al. (1995) Gene Ther 2: 336–343. Non-viral vectors which are also suitable include DNA-lipid complexes, for example liposome-mediated or ligand/poly-L-Lysine conjugates, such as asialoglyco-protein-mediated delivery systems. See, for example: Feigner et al. (1994) J. Biol. Chem, 269: 2550–2561; Derossi et al. (1995) Restor. Neurol. Neuros. 8: 7–10; and Abcallah et al. (1995) Biol. Cell 85: 1–7.

If a vector is chosen as the delivery vehicle for the gene, it may be any vector which allows expression of the gene in the host cells. It is preferable if the vector also is one that is capable of integrating into the host genome, so that the gene can be expressed permanently. Ad (adenovirus) vectors have been exploited for the delivery of foreign genes to cells for a number of reasons, including the fact that Ad vectors have been shown to be highly effective for the transfer of genes into a wide variety of tissues in vivo and the fact that Ad infects both dividing and non-dividing cells. The vector is administered to the host, generally by intravenous injection. Suitable titers will depend on a number of factors, such as the particular vector chosen, the host, strength of promoter used and the severity of the disease being treated.

Alternatively, it is contemplated that in some human disease states, preventing the expression of, or decreasing the activity of, the human FKHL14/FOXC2 gene will be useful in treating disease states. It is contemplated that antisense therapy or gene therapy could be applied to negatively regulate the expression of the human FKHL14/FOXC2 gene. Antisense nucleic acids (preferably 10 to 20 base-pair oligonucleotides) capable of specifically binding to FKHL14/FOXC2 expression control sequences or FKHL14/FOXC2 RNA are introduced into cells (e.g. by a viral vector or colloidal dispersion system such as a liposome). The antisense nucleic acid binds to the FKHL14/FOXC2 target nucleotide sequence in the cell and prevents transcription and/or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5'-end. Suppression of FKHL14/FOXC2 expression at either the transcriptional or translational level is useful to generate cellular or animal models for diseases/conditions characterized by aberrant FKHL14/FOXC2 expression.

Throughout this description the terms "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

EXPERIMENTAL METHODS

Cloning and DNA Construct

A human adipose tissue λgt11 cDNA library (Clontech) was screened with a probe mixture corresponding to the conserved fork-head domain derived from: FOXC1, FOXD1, FOXL1, and FOXA1. Hybridization was carried out at low stringency, i.e. 6×SSC at +60° C., post-hybridization washes at 0.5×SSC at +60° C. One of the positive recombinants harboring a 2.1 kb insert was subcloned and sequenced. A 5.4-kb EcoRV-SmaI fragment was excised from pBluescript II SK(+) vector containing the 5.4-kb promoter/enhancer of the mouse aP2 gene and ligated into the EcoRV-SpeI blunt site of pBluescript II SK(+) vector containing the 2.1 kb FOXC2 cDNA. A 7.6 kb XhoI blunt fragment containing the aP2 promoter/enhancer followed by the FOXC2 cDNA was excised from the above plasmid and ligated into the EcoRV site of the pCB6+ vector, which contains a polyadenylation signal from the human growth hormone gene. After these procedures the resulting 8.2-kb fragment, harboring the aP2-FOXC2 construct with polyadenylation signal, was flanked by the unique sites NotI and AgeI. The plasmid was sequenced over ligation sites.

Transgenic Mice

Construct DNA (aP2-FOXC2), purified using Qiagen kit, according to manufacturer's instructions, was injected into the male pronucleus of (C57BL6×CBA) $F_1$ zygotes, cultured over night and transferred to pseudopregnant females. Tg founder lines were back-crossed to C57BL6/J for four generations. Mice were feed a standard chow with 4% fat content. In experiments with high fat diet mice were fed either a chow with 58% fat or a control diet with 11.4% fat (on a caloric basis; Research Diets) for 7 weeks. High fat chow has a total energy content of 23.4 KJ/g, control diet 12.6 KJ/g.

Histology

Tissues were fixed over night in 4% paraformaldehyde in PBS at +4° C., dehydrated, embedded in paraffin, sectioned (6–8 μm) and stained with haematoxylin and eosin.

Serum and Lipid Analysis

Plasma insulin was determined radioimmunochemically with the use of a guinea pig anti-rat insulin antibody, $^{125}$I-labeled porcine insulin as tracer and rat insulin as standard (Linco). Free and bound radioactivity was separated by use of an anti-IgG (goat anti-guinea pig) antibody (Linco). The sensitivity of the assay is 17 pmol/l and the coefficiency of variation is less than 3% at both low and high levels. Plasma glucose was determined with the glucose oxidase method and FFA was measured photometrically. Plasma glucagon was determined radioimmunochemically with the use of a guinea pig antiglucagon antibody specific for pancreatic glucagon, $^{125}$I-labelled-glucagon as tracer, and glucagon standard (Linco). Free and bound radioactivity was separated by use of an anti-IgG (goat anti-guinea pig) antibody (Linco). The sensitivity of the assay is 7.5 μg/ml and the coefficient of variation is less than 9%. Blood levels of serum cholesterol and triglycerides were determined by fully enzymatic techniques 39,40. Total body lipid was assessed using alcoholic hydroxide digestion with saponification of all lipids, neutralization, followed by enzymatic determination of glycerol.

Intravenous Glucose Tolerance Test

The mice were anesthetized with an intraperitoneal injection of midazolam 0.4 mg/mouse (Hoffman-La-Roche) and a combination of fluanison (0.9 mg/mouse) and fentanyl 0.02 mg/mouse (Janssen). Thereafter, a blood sample was taken from the retrobulbar, intraorbital, capillary plexus in heparinized tubes, and D-glucose 1 g/kg L(British Drug Houses) was injected rapidly intravenously. New blood samples were taken after 1, 5, 20, and 50 minutes. Following immediate centrifugation at +4° C., plasma was separated and stored at −20° C. or until analysis.

Northern Blot cDNA probes for mouse FoxC2, aP2, ADD-1/SREBP1, coxII, adipsin, $β_{1-3}$-AR, GLUT4, IR, IRS1, and IRS2 were prepared by RT-PCR by use of first-strand cDNA from mouse epididymal fat poly(A)$^+$ RNA. The PCR primers used to generate these probes were as follows:

FoxC2: 5' primer, GCTTCGCCTCCTCCATGGGAA (SEQ ID NO:3) and 3' primer, GGTTACAAATCCG-CACTCGTT (SEQ ID NO:4) (GenBank #Y08222).

aP2: 5' primer, CTC CTG TGCTGCAGCCTTTCTC (SEQ ID NO:5) and 3' primer, CGTAACTCACCAC-CACCAGCTTGTC (SEQ ID NO:6) (GenBank #M13261).

ADD1/SREBP-1: 5' primer, GCCAACTCTCCT-GAGAGCTT (SEQ ID NO:7) and 3' primer, CTCCT-GCTTGAGCTTCTGGTT (SEQ ID NO:8) (GenBank #AB017337).

CoxII: 5' primer, CCATTCCAACTTGGTCTACAA (SEQ ID NO:9) and 3' primer, GGAACCATTTCTAG-GACAATG (SEQ ID NO:10) (GenBank #J01420).

Adipsin: 5' primer, CGAGGCCGGATTCTGGGTGGC-CAG (SEQ ID NO:11) and 3' primer, TCGATCCA-CATCCGGTAGGATG (SEQ ID NO:12) (GenBank #X04673).

$β_1$-AR: 5' primer, CGGCTGCAGACGCTCACCAA (SEQ ID NO:13) and 3' primer, CGCCACCAGTG-CATGAGGAT ((SEQ ID NO:14) GenBank #L10084).

$β_2$-AR: 5' primer, GCTGCAGAAGATAGACAAAT (SEQ ID NO:15) and 3' primer, GGGATCCTCACA-CAGCAGTT (SEQ ID NO:16) (GenBank #X15643).

β₃-AR: 5' primer, CTGCTAGCATCGAGACCTT (SEQ ID NO:17) and 3' primer, CGAGCATAGACGAAGAGCAT (SEQ ID NO:18) (GenBank #X60438).

GLUT4: 5' primer,CTCAGCAGCGAGTGACTGGGAC (SEQ ID NO:19) and 3' primer, CCCTGAGTAGGCGCCAATGAGG (SEQ ID NO:20) (GenBank #D28561).

IR: 5' primer, GTAGCCTGATCATCAACATCCG (SEQ ID NO:21) and 3' primer, CCTGCCCATCAAACTCTGTCAC (SEQ ID NO:22) (GenBank #J05149).

IRS 1: 5' primer, ATGGCGAGCCCTCCGGATACCG (SEQ ID NO:23) and 3' primer, CCTCTCCAACGCCAGAAGCTGCC (SEQ ID NO:24) (GenBank #X69722).

IRS2: 5' primer, GGATAATGGTGACTATACCGAGA (SEQ ID NO:25) and 3' primer, CTCACATCGATGGCGATATAGTT (SEQ ID NO:26) (GenBank #AF090738).

cDNA probes were radiolabeled with [α-³²P]dCTP (3000 Ci/mmole) by the random labeling method. Total RNA from mice in each group was pooled, and aliquots of 12 μg were separated on an agarose gel. The filters were hybridized with ³²P-labeled probe (10⁶ cpm/ml) for 1 h at 62° C. with QuikHyb solution (Stratagene) and washed with 0.1% SDS/ 0.1×SSC at +62° C. for 3×20 min.

Transfections and Reporter Gene Analysis

Non-confluent cultures of 3T3-L1 adipocytes were transfected with a CAT reporter (pCAT) driven by the human RIα proximal promoters upstream of the alternatively spliced 1a and 1b leader exons (nucleotides 1509 to 2470 GenBank #Y07641). To control transfection efficiency a pGL3control (Promega) luciferase-encoding vector was used. In cotransfections a FOXC2 expression vector or vector void of insert was used. Transfections were carried out using lipofectamine (Gibco), followed by CAT and luciferase assays.

PKA Immunoblotting and Kinase Activity

WAT and BAT were treated by a Polytron tissue homogenizer (3×15 s) and sonicated, on ice, in a buffer containing 10 mM potassium phosphate, pH 6.8, 150 mM sodium chloride, 1 mM EDTA, 10 mM CHAPS and protease inhibitors, and centrifuged (15,000×g) to remove insoluble material. Protein concentrations were determined by Bradford assays (BioRad). For immunoblotting, 30 μg of protein was separated by 10% SDS-PAGE, transferred to PVDF membranes and incubated with anti-RIα and anti-RIIβ mAb. Primary antibodies were detected by HRP-conjugated anti-mouse IgG (Transduction Laboratories, 1:5000) and ECL (Amersham). PKA activity was measured using Kemptide (Leu-Arg-Arg-Ala-Ser-Leu-Gly) as substrate in the absence or presence of varying concentrations of cAMP. The low levels of activity not inhibited by PKI (2 μM) were subtracted to determine PKA-specific activity.

EXAMPLES OF THE INVENTION

Example 1

Isolation of FKHL14/FOXC2 From Human Abdominal Fat Tissue

Figure 3A:
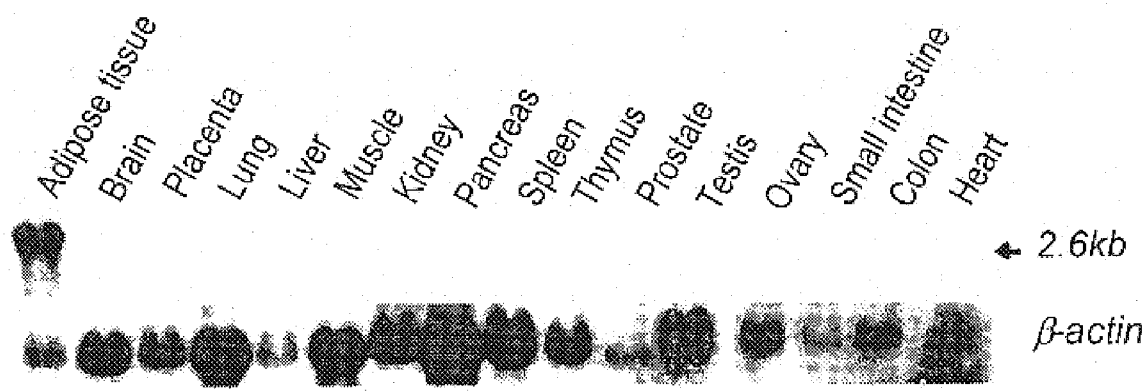
Figure 3B:
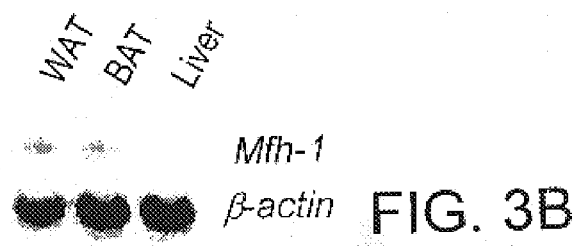

To identify presumptive winged helix genes that are expressed in adipose tissue we screened a Human Fat Cell 5'-STRETCH plus cDNA Library (Clontech) using a low stringency hybridization strategy with a mix of cDNA probes corresponding to DNA-binding domains from different winged helix proteins, to cover the variation between different family members. By this technique, we were able to identify three different forkhead genes, namely FKHL5, FKHL14, and FKHL18. FKHL5 was known to be expressed exclusively in lung and placenta (Pierrou et al., 1994) and expression in adipose tissue could not be detected as judged by Northern blot analysis (data not shown). FKHL18 was identified as a novel member of the forkhead family (Cederberg et al., 1997) having a very high homology with the forkhead motif of the mouse gene fkh-3 (Kaestner et al., 1993). Sequence from outside the forkhead motif have not yet been published for fkh-3 but with regard to the discrepancy of the expression patterns, with FKHL18 being expressed in arterial vessel wall (aorta) and to a lower extent in kidney and fkh-3 being expressed in a wide variety of tissues, they are presumed to constitute two different genes. We were not able to detect any expression of FKHL18 in adipose tissue (data not shown). The third gene that was identified, FKHL14/FOXC2, (Miura, N. et al. (1997) Genomics 41, 489–492) was shown to be expressed exclusively in human adult adipose tissue by Northern blot analysis (FIG. 3a). The mouse homologue of FKHL14/FOXC2 is known as Mfh1 (also known as Foxc2), and is expressed in dynamic patterns in the paraxial mesoderm of the trunk and head, in the mesenchyme and endothelial cells of the branchial arches, and in many other sites in the embryo (Kaestner et al., 1996; Miura et al., 1993; Winnier et al., 1997). It has been demonstrated by gene targeting experiments that Mfh1 plays a crucial role during embryonic development. Homozygous null mutants died pre- and perinatally with multiple skeletal and cardiovascular defects, including defects in the neurocranium and vertebral column, interruptions or coarctations of the aortic arch, and ventricular septal defects (Iida et al., 1997; Winnier et al., 1997). Heterozygous mice were indistinguishable from wild-type and appeared healthy. The expression of Mfh1 in adult tissues was restricted to WAT and BAT (FIG. 3).

Example 2

FKHL14/FOXC2 Represses Ob Gene Expression in vitro

To be able to study the function of the FKHL14/FOXC2 protein in vitro we prepared an expression construct containing the full length FKHL14/FOXC2 cDNA sequence (SEQ ID NO: 1) inserted into the expression plasmid pCB6+ (Brewer, 1994). This construct could then be used for transient transfection assays in mammalian cell culture systems to elucidate the action of FKHL14/FOXC2 protein on promoters for different genes involved in adipocyte differentiation and development. To investigate the Ob promoter we used a Chinese hamster ovary (CHO) cell line (the promoter is known to be active in these cells). Transient co-transfections were performed using a 6.5-kb fragment of the Ob promoter coupled to the luciferase gene used as a reporter. A tenfold down-regulation of the activity of the Ob promoter was observed then co-transfected with FKHL14/FOXC2 expression plasmid (FIG. 4).

Example 3

Generation of Transgenic Mice Overexpressing FKHL14

Figure 5B:
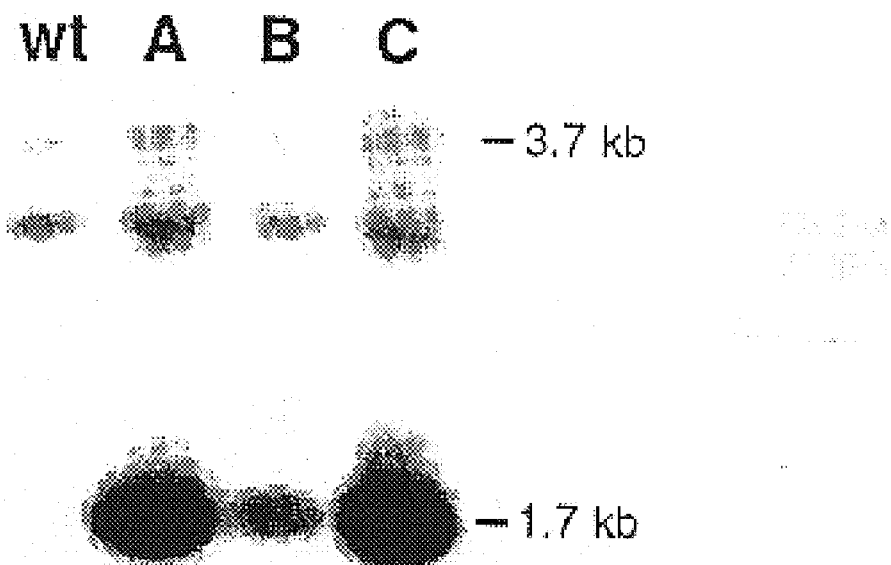

To elucidate whatever function FKHL14/FOXC2 might have in vivo we decided to create transgenic mice overexpressing FKHL14/FOXC2 in adipose tissue. To achieve overexpression of FKHL14/FOXC2 in both white and brown adipose tissue, we prepared a transgene construct (FIG. 5a) encoding FKHL14/FOXC2 driven by a 5.4-kb DNA fragment containing the adipose-specific enhancer/promoter of the gene encoding adipocyte P2 (Ross et al., 1990). Integration positive mice were identified using Southern blot analysis (FIG. 5b).

Figure 6:
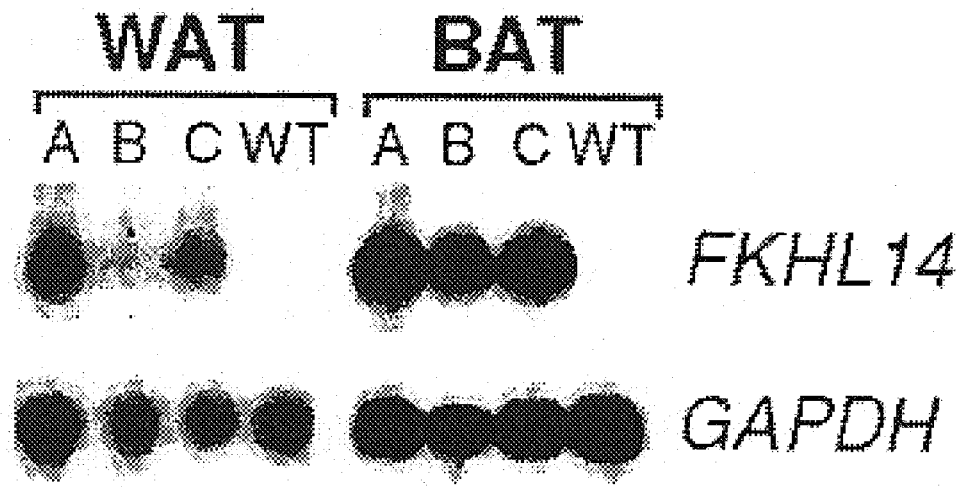

We studied three lines of transgenic mice (A, B, and C) that were derived from independent founders. Transgene expression, analyzed by Northern blot using a FKHL14/FOXC2 (human specific) probe, was detected at high levels in both WAT and BAT for all three founders. The three different founders had a slight difference in expression levels of the transgene in white fat, founder A having the highest and founder B the lowest, while the expression levels in brown fat were equal (FIG. 6). All of the transgenic mice used for the study were hemizygous for the transgene and from the second to fourth generation. The transgenic mice appeared normal at external inspection and the transgenic allele was propagated with the expected mendelian distribution. Fed a standard rodent chow diet (4% fat, 18.5% protein, and 55.7% sucrose) weight gain was studied for all founders from 4 weeks up to 6 months of age with no significant difference between nontransgenic and transgenic littermates noticed (data not shown).

Example 4

WAT of FKHL14/FOXC2 Transgenic Mice Morphologically Resembles BAT

Figures 7A, 7B:
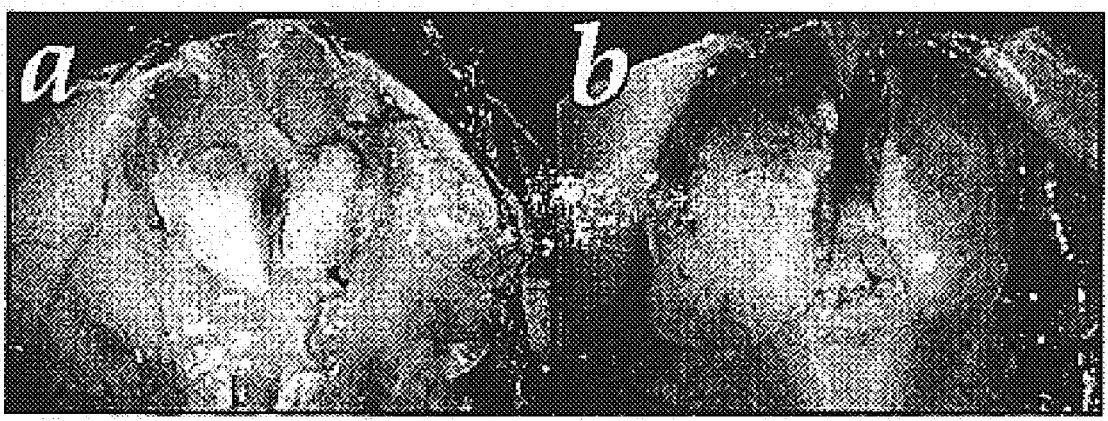
Figures 7C, 7D:
Figures 7E, 7F:
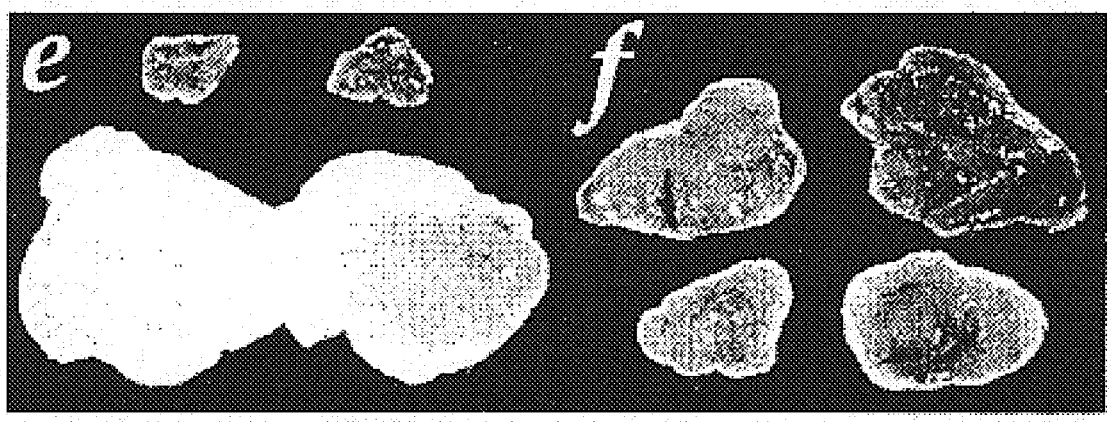
Figure 8C:
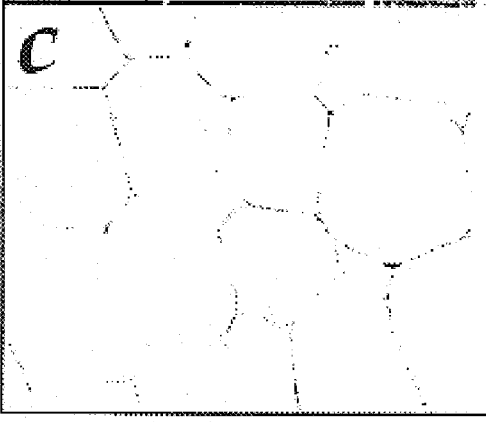
Figure 8D:
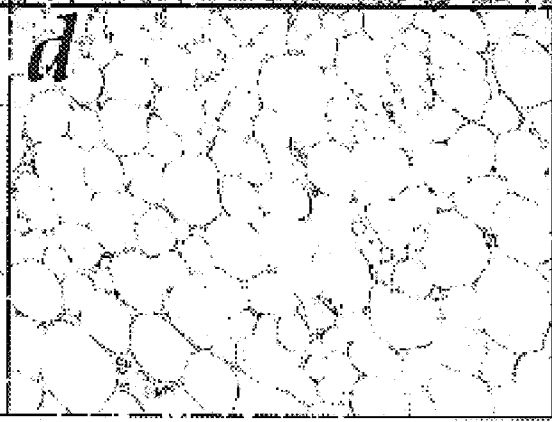

The interscapular brown adipose tissue depot and the intrabdominal white adipose tissue were examined in 5-months-old mice (FIG. 7). Interscapulary, transgenic mice had a greatly enlarged bilobed (dissected apart in the picture) fat pad with the "looks" of brown adipose tissue without the usual coverage of white adipose tissue (FIG. 7b), which normally have to be dissected to uncover the interscapular BAT depot (FIG. 7a). An exposed abdominal view of FKHL14/FOXC2 transgenic mice revealed an obvious decrease of intrabdominal fat mass and also a distinct change in the appearance towards the brown adipose tissue phenotype (FIG. 7d), when compared to the large, pale lipid-storing intrabdominal fat pad of wild-type mice (FIG. 7c). The adipose tissue change in appearance and mass between transgenic and nontransgenic mice was very striking then the depots had been dissected out (FIGS. 7e & f). Histological analysis of BAT and WAT from 5-months-old mice revealed profound differences between transgenic and nontransgenic tissues. The majority of adipocytes in brown fat of the transgenic mice contained few markedly enlarged fat droplets (FIG. 8b), instead of small multilocular fat droplets typical for BAT (FIG. 8a). Adipocytes in intrabdominal white fat of the transgenic mouse showed heterogeneity of size, all of them having a clearly reduced size (FIG. 8d). This was in contrast to WAT from wild-type mouse, which consisted of large adipocytes of uniform size filled with a large, unilocular lipid-storing vacuole (FIG. 8c).

Figure 9C:
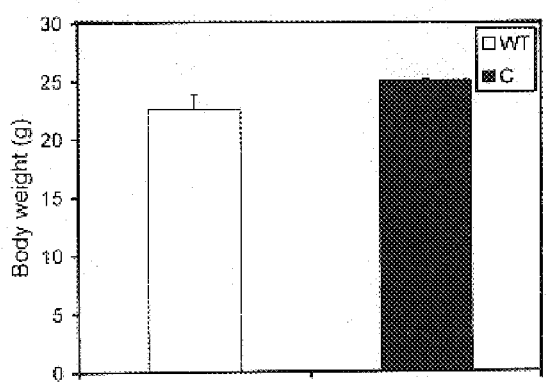
Figure 9D:
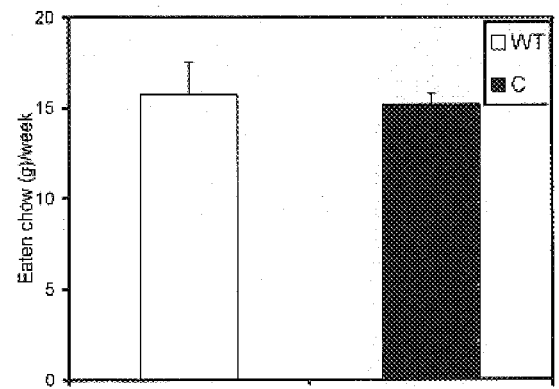

To further examine the change of size of fat depots in transgenic mice, we compared the weights of intrabdominal WAT depots and interscapular BAT depots of 5-months-old wild-type females (n=3) and FKHL14/FOXC2 transgenic littermates (n=3). In transgenic mice there was a decrease in weight of the intrabdominal WAT depot (~40%) whereas the interscapular BAT depot showed a marked increase (~7.5 times; FIG. 9a). In consequence the ratio between weights of the intrabdominal fat depot and the interscapular brown fat depot was greatly decreased (FIG. 9b). No significant difference in body weight could be detected between transgenic and nontransgenic mice (FIG. 9c), nor could any difference in food consumption be observed then measured during a time period of two months (FIG. 9d).

Example 5

Altered Gene Expression in FKHL14/FOXC2 Transgenic Mice

FIG. 10 shows an analysis of mRNA steady state levels in white and brown adipose tissue of wild-type mice and the three independent transgenic founders. In wild-type mice, the mRNA for uncoupling protein 1 (UCP1) was detectable only in BAT, but in the transgenic mice expression could be detected in WAT, in a dose responsive manner in proportion to the expression level of transgenic FKHL14. The WAT blot and BAT blot had different exposure times, 2 days and 30 minutes respectively. UCP2 seemed to have a tendency to be regulated in the opposite direction as compared with UCP1 in WAT of transgenic mice. The uncoupling protein expressed in skeletal muscle and BAT, UCP3, showed greatly decreased levels in transgenic BAT. The cytochrome c-oxidase subunit II (CoxII), a gene encoded by the mitochondrial genome, was used as a marker for density of mitochondria. The density of mitochondria in WAT and BAT from transgenic animals appeared to be elevated and to a lesser extent reduced, respectively. In wild-type mice, the mRNAs of $\beta_1$- and $\beta_3$-AR were much lower in WAT than in BAT. The FKHL14/FOXC2 transgene abolished this discrepancy, raising these mRNAs selectively in WAT so that they became equal, or in the case of $\beta_3$-AR even higher, compared to the levels in BAT. The $\beta_2$-AR mRNA level was elevated in both WAT and BAT of transgenic mice, reaching levels not seen in nor WAT or BAT of wild-type littermates. White fat depots of transgenic animals exhibited profound increment in four of its mRNAs that are associated with fully differentiated adipocytes, that is, PPARγ2, C/EBPα, aP2, and adipsin. Furthermore PGC-1, a co-activator of PPARγ2, was upregulated in both WAT and BAT. The mRNA for ADD1/SREBP1 was elevated in WAT for all three founders. The transgenic animals demonstrated a reduction of the amount of leptin mRNA with the most distinct effect in BAT. Steady state levels of LPL mRNA appear to have increased slightly in WAT of transgenic mice. All investigated markers involved in insulin action were upregulated: the insulin receptor (InsR), IRS-1, IRS-2, and insulin-responsive glucose transporter-4 (GLUT4). The upregulation was most evident in WAT. GAPDH was used as a control to verify equal amounts of total RNA in the different lanes.

Example 6

Triglyceride Content is Altered in FKHL14/FOXC2 Transgenic Mice

Figure 11:
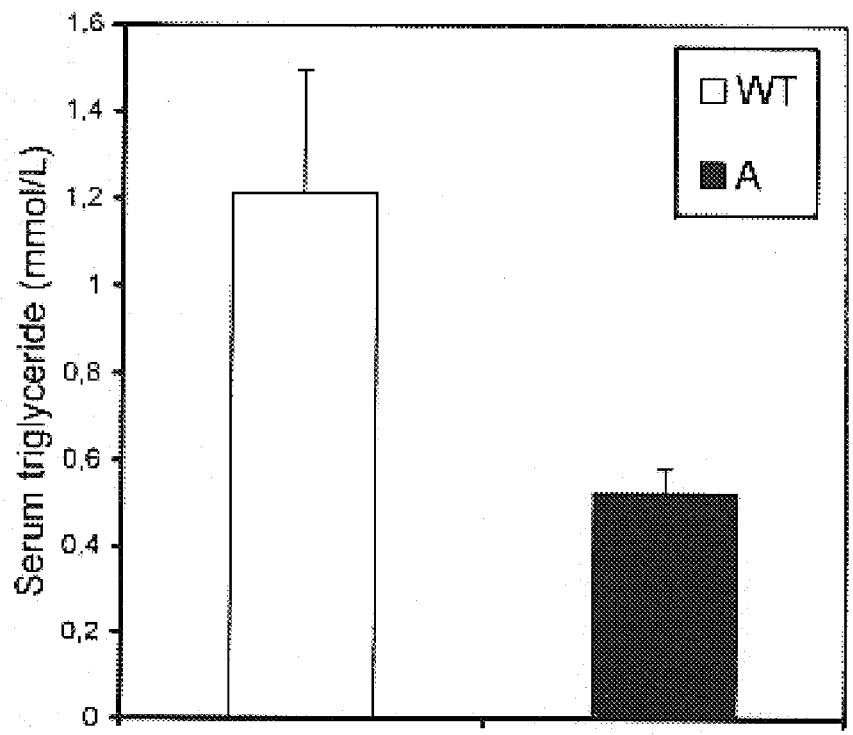

Serum triglyceride content was analysed for 14-weeks-old wild-type males (n=4) and FKHL14/FOXC2 transgenic littermates (n=4) fed ad libitum. The transgenic animals exhibited a ~60% reduction in serum triglyceride levels (FIG. 11).

Total body lipid content was assessed using alcoholic potassium hydroxide digestion with saponification of all fats, neutralization, and then enzymatic determination of glycerol (Triglyceride kit, Sigma) as described previously (Salmon and Flatt, 1985). The assay was carried out for 6-months-old wild-type males (n=4) and FKHL14/FOXC2 transgenic littermates (n=4) fed ad libitum. The total body lipid content was reduced to 10% of the body weight for transgenic mice compared with the normal 30% of body lipid noted for wild-type mice (FIG. 12).

Example 7

Figure 13A:
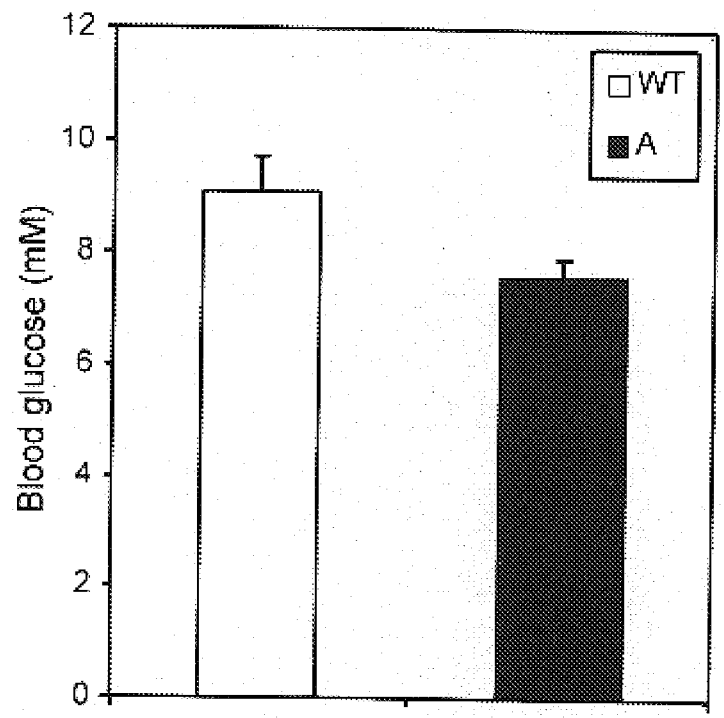

Lower Blood Glucose and More Efficient Glucose Elimination in FKHL14/FOXC2 Transgenic Mice Nonfasting blood glucose levels were measured for 10-weeks-old wild-type males and females (n=5+5), and FKHL14/FOXC2 transgenic littermates (n=5+5) fed ad libitum. The transgenic animals showed a significant 16% reduction in nonfasting blood glucose levels (FIG. 13a).

Figure 13B:
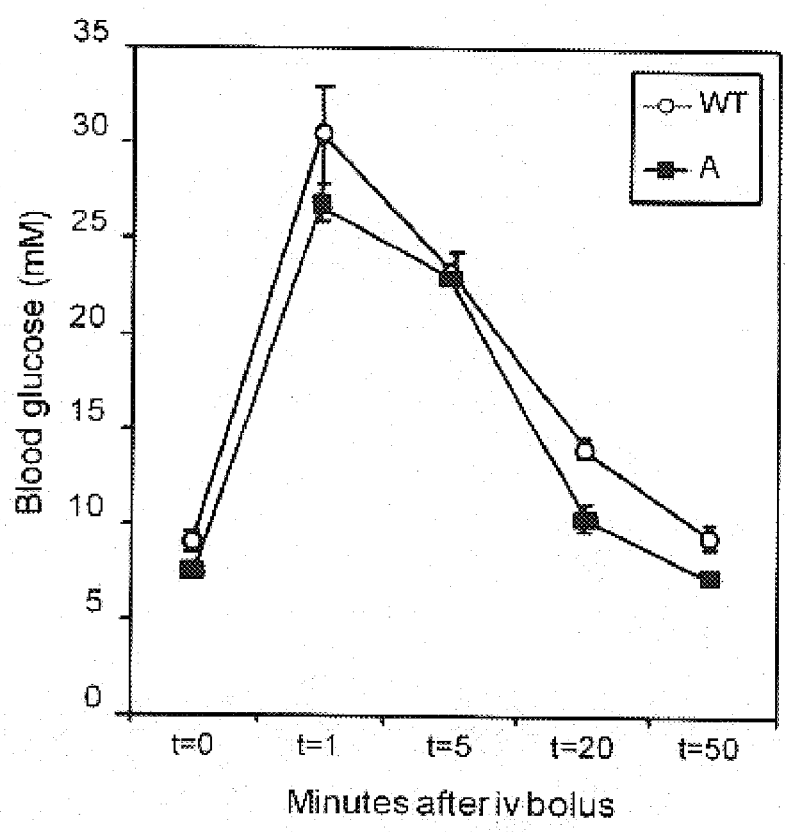

A glucose tolerance test was performed on 10-weeks-old wild-type males and females (n=5+5) and FKHL14/FOXC2 transgenic littermates (n=5+5) fed ad libitum. Plasma glucose levels peaked at one minute after intravenous glucose administration, and thereafter plasma glucose levels returned to baseline levels within the 50-minutes study period. Transgenic mice displayed an enhanced glucose elimination, with plasma glucose levels significantly lower than wild-type littermates at 0, 20, and 50 minutes (P<0.05; P<0.001; P<0.05) (FIG. 13b). Data are means of both males and females as no difference between gender was noticed.

Example 8

Increased Insulin Sensitivity in FKHL14/FOXC2 Transgenic Mice

Figure 14A:
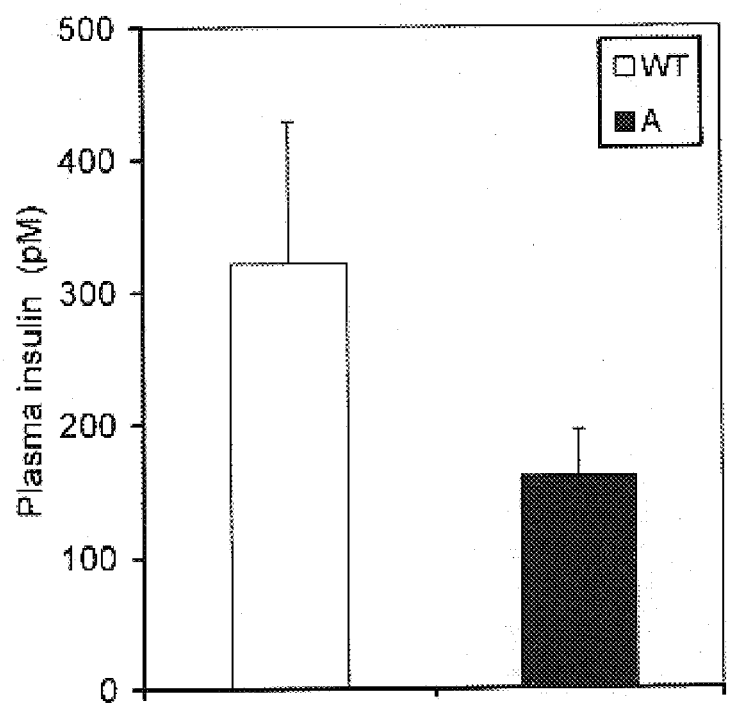
Figure 14B:
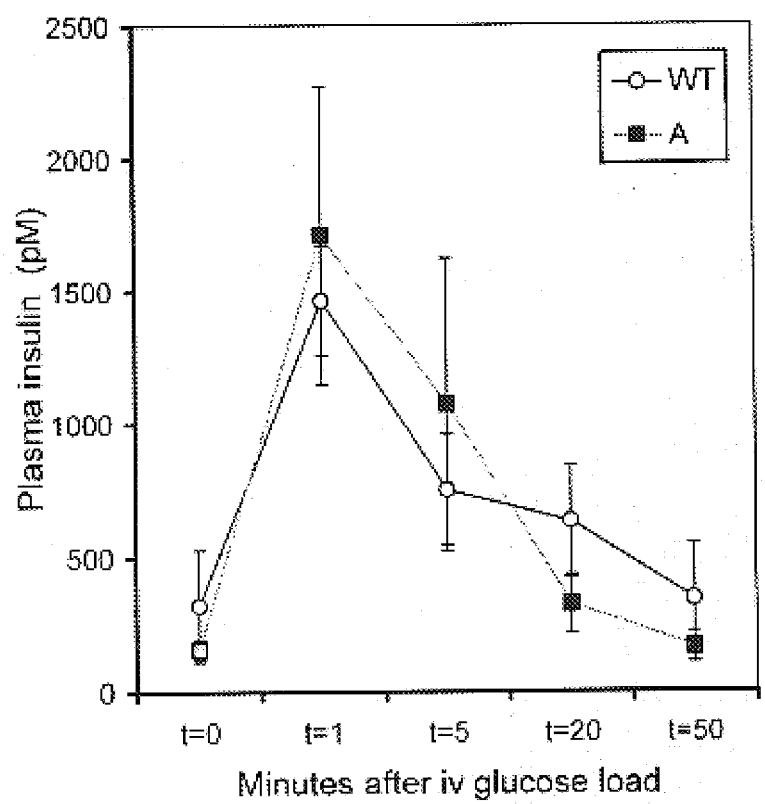
Figure 14C:
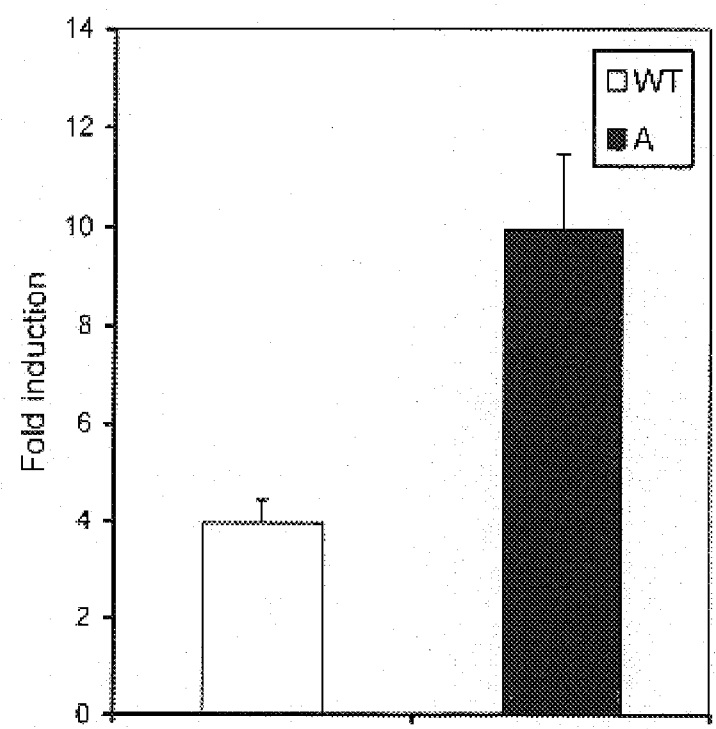

Non-fasting plasma insulin levels in FKHL14/FOXC2 transgenic mice were analyzed using the same group of animals as was used for blood glucose measurements. The concentration of plasma insulin in FKHL14/FOXC2 transgenic mice before the start of the glucose tolerance test were reduced to ~50% of the levels registered for wild-type littermates (FIG. 14a). The rapid intravenous injection of glucose (1 g/kg) raised plasma insulin levels 4-fold in wild-type mice and 10-fold in FKHL14/FOXC2 transgenic littermates after one minute (FIG. 14c). Thereafter, plasma insulin levels rapidly returned toward baseline values observed before the glucose load, with transgenic mice having significantly lower levels at 20 and 50 minutes (P<0.05; P<0.05) (FIG. 14b). Data are means of both males and females as no difference between gender was noticed.

Figure 16A:
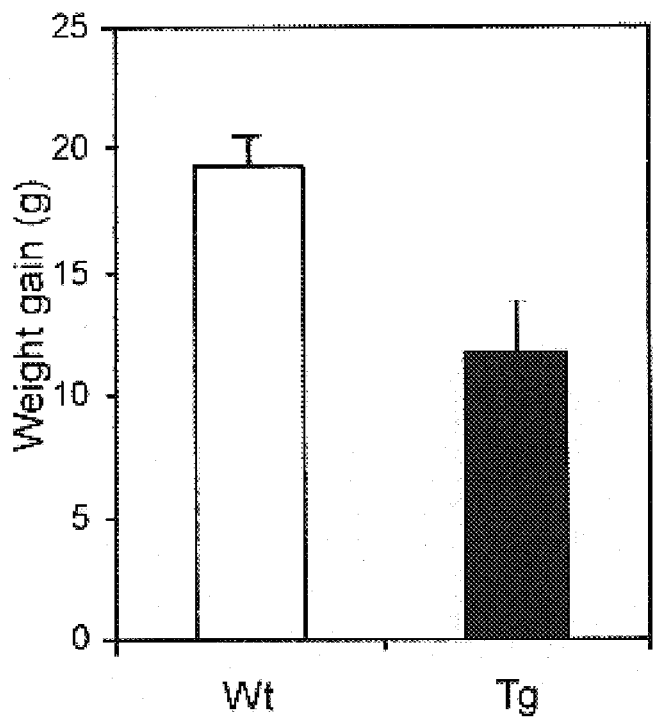
Figure 16B:
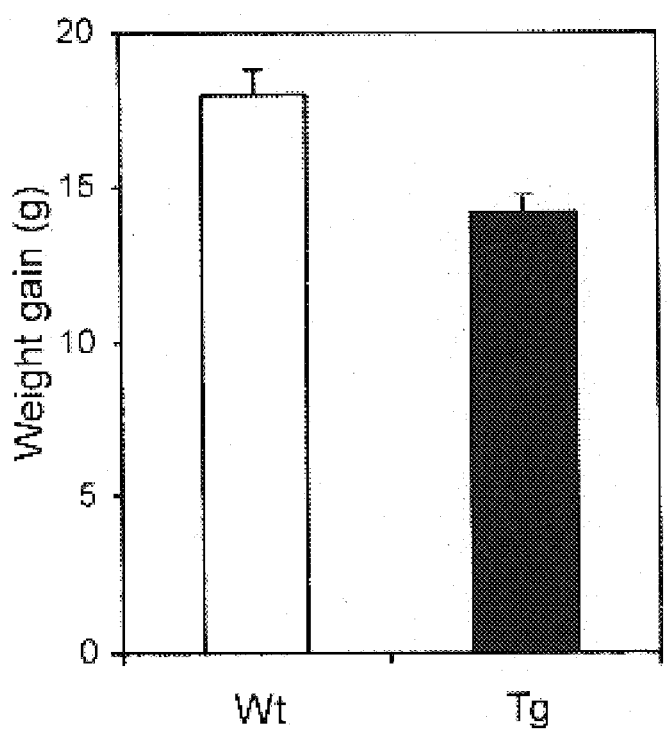

In mice on a high fat diet, there are significantly lower weight gains in transgenic mice as compared with wt. In females the weight gain is 39% (p<0.02; FIG. 16a) lower as compared with wt females and for males the difference is 21% (p<0.03; FIG. 16b). These findings highlight FKHL14/FOXC2, not only as a gene of importance for adipose tissue distribution, morphology and gene expression profile, but also, more importantly, as a major regulator of general lipid and glucose metabolism including protection against diet induced weight gains.

Example 9

Interaction Trap/Two-hybrid System

In order to assay for polypeptides interacting with the FKHL14/FOXC2 polypeptide, the interaction trap/two-hybrid library screening method can be used. This assay was first described in Fields & Song (1989) Nature 340, 245–246. Kits are available from Clontech, Palo Alto, Calif. (Matchmaker Two-Hybrid System 3).

A fusion of an FKHL14/FOXC2 nucleotide sequence and the yeast transcription factor GAL4 DNA-binding domain (DNA-BD) is constructed in an appropriate plasmid (e.g. pGBKT7) using standard subcloning techniques. Similarly, a GAL4 active domain (AD) fusion library is constructed in a second plasmid (ie. pGADT7) from cDNA of potential binding proteins. The DNA-BD fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity.

Yeast cells are transformed (ca. $10^5$ transformants/mg DNA) with both the DNA-BD and library fusion plasmids according to standard procedures. In vivo binding of DNA-BD/(FKHL14/FOXC2) with AD/library proteins results in transcription of specific yeast plasmid reporter genes (i.e., lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-β-D-galactoside) supplemented media (filter assay for β-galactosidase activity is described in Breeden, et al. (1985) Cold Spring Harb. Symp. Quant. Biol. 50, 643). Positive AD-library plasmids are rescued from transformants and reintroduced into the original yeast strain as well as other strains containing unrelated DNA-BD fusion proteins to confirm specific (FKHL14/FOXC2)/library protein interactions. Insert DNA is sequenced to verify the presence of an open reading frame fused to GAL4 AD and to determine the identity of the binding protein.

Example 10

Mobility Shift DNA-Binding Assay

A gel electrophoresis mobility shift assay, according to standard procedures, can rapidly detect specific protein-DNA interactions. Probe DNA (<300 bp) is obtained from synthetic oligonucleotides, restriction endonuclease fragments, or PCR fragments and end-labeled with 32p An aliquot of purified FKHL14/FOXC2 (ca. 15 µg) or crude FKHL14/FOXC2 extract (ca. 15 ng) is incubated at constant temperature (in the range 22–37° C.) for at least 30 minutes in 10–15 µl of buffer (i.e. TAE or TBE, pH 8.0–8.5) containing radiolabeled probe DNA, nonspecific carrier DNA (ca. 1 µg), BSA (300 µg/ml), and 10% (v/v) glycerol. The reaction mixture is then loaded onto a polyacrylamide gel and run at 30–35 mA until good separation of free probe DNA from protein-DNA complexes occurs. The gel is then dried and bands corresponding to free DNA and protein-DNA complexes are detected by autoradiography.

Example 11

Reporter Gene Assay to Identify Modulating Compounds

Reporter gene assays are well known as tools to signal transcriptional activity in cells. (For a review of chemiluminescent and bioluminescent reporter gene assays, see Bronstein et al. (1994) Analytical Biochemistry 219, 169–181.) For instance, the photoprotein luciferase provides a useful tool for assaying for modulators of FKHL14/FOXC2 activity. Cells (e.g., CHO cells or COS 7 cells) are transiently cotransfected with both a FKHL14/FOXC2 expression construct and a reporter construct which includes a gene for the luciferase protein downstream from a transcription factor binding site. Agonist binding to FKHL14/FOXC2 results in expression of the luciferase gene. Luciferase activity may be quantitatively measured using e.g. luciferase assay reagents that are commercially available from Promega (Madison, Wis.). Differences in luminescence in the presence versus the absence of a candidate modulator compound are indicative of modulatory activity.

REFERENCES

Ailhaud, G., Grimaldi, P., and Negrel, R. (1992). Cellular and molecular aspects of adipose tissue development. *Annu Rev Nutr* 12, 207–33.

Arch, J. R., and Wilson, S. (1996). Prospects for beta 3-adrenoceptor agonists in the treatment of obesity and diabetes. *Int J Obes Relat Metab Disord* 20, 191–9.

Barak, Y., Nelson, M. C., Ong, E. S., Jones, Y. Z., Ruiz-Lozano, P., Chien, K. R., Koder, A., and Evans, R. M. (1999). PPAR gamma is required for placental, cardiac, and adipose tissue development. *Mol Cell* 4, 585–95.

Bloom, J. D., Dutia, M. D., Johnson, B. D., Wissner, A., Burns, M. G., Largis, E. E., Dolan, J. A., and Claus, T. H. (1992). Disodium (R,R)-5-[2-[[2-(3-chlorophenyl)-2-hydroxyethyl]-amino]propyl]-1,3-benzodioxole-2,2-dicarboxylate (CL 316,243). A potent beta-adrenergic agonist virtually specific for beta 3 receptors. A promising antidiabetic and antiobesity agent. *J Med Chem* 35, 3081–4.

Boss, O., Samec, S., Paoloni-Giacobino, A., Rossier, C., Dulloo, A., Seydoux, J., Muzzin, P., and Giacobino, J. P. (1997). Uncoupling protein-3: a new member of the mitochondrial carrier family with tissue-specific expression. *FEBS Lett* 408, 39–42.

Brewer, C. B. (1994). Cytomegalovirus plasmid vectors for permanent lines of polarized epithelial cells. *Methods Cell Biol* 43, 233–45.

Brown, M. S., and Goldstein, J. L. (1997). The SREBP pathway: regulation of cholesterol metabolism by proteolysis of a membrane-bound transcription factor. *Cell* 89, 331–40.

Cao, Z., Umek, R. M., and McKnight, S. L. (1991). Regulated expression of three C/EBP isoforms during adipose conversion of 3T3-L1 cells. *Genes Dev* 5, 1538–52.

Cawthorne, M. A., Sennitt, M. V., Arch, J. R., and Smith, S. A. (1992). BRL 35135, a potent and selective atypical beta-adrenoceptor agonist. *Am J Clin Nutr* 55, 252S–257S.

Cederberg, A., Betz, R., Lagercrantz, S., Larsson, C., Hulander, M., Carlsson, P., and Enerback, S. (1997). Chromosome localization, sequence analysis, and expression pattern identify FKHL 18 as a novel human forkhead gene. *Genomics* 44, 344–6.

Champigny, O., and Ricquier, D. (1996). Evidence from in vitro differentiating cells that adrenoceptor agonists can increase uncoupling protein mRNA level in adipocytes of adult humans: an RT-PCR study. *J Lipid Res* 37, 1907–14.

Choy, L. N., and Spiegelman, B. M. (1996). Regulation of alternative pathway activation and C3a production by adipose cells. *Obes Res* 4, 521–32.

Christy, R. J., Yang, V. W., Ntambi, J. M., Geiman, D. E., Landschulz, W. H., Friedman, A. D., Nakabeppu, Y., Kelly, T. J., and Lane, M. D. (1989). Differentiation-induced gene expression in 3T3-L1 preadipocytes: CCAAT/enhancer binding protein interacts with and activates the promoters of two adipocyte-specific genes. *Genes Dev* 3, 1323–35.

Chua, S. C., Jr., Chung, W. K., Wu-Peng, X. S., Zhang, Y., Liu, S. M., Tartaglia, L., and Leibel, R. L. (1996). Phenotypes of mouse diabetes and rat fatty due to mutations in the OB (leptin) receptor. *Science* 271, 994–6.

Cianflone, K., Maslowska, M., and Sniderman, A. (1995). The acylation stimulating protein-adipsin system. *Int J Obes Relat Metab Disord* 19 Suppl 1, S34–8.

Coleman, D. L. (1973). Effects of parabiosis of obese with diabetes and normal mice. *Diabetologia* 9, 294–8.

Cornelius, P., MacDougald, O. A., and Lane, M. D. (1994). Regulation of adipocyte development. *Annu Rev Nutr* 14, 99–129.

Cousin, B., Cinti, S., Morroni, M., Raimbault, S., Ricquier, D., Penicaud, L., and Casteilla, L. (1992). Occurrence of brown adipocytes in rat white adipose tissue: molecular and morphological characterization. *J Cell Sci* 103, 931–42.

Cummings, D. E., Brandon, E. P., Planas, J. V., Motamed, K., Idzerda, R. L., and McKnight, G. S. (1996). Genetically lean mice result from targeted disruption of the RII beta subunit of protein kinase A. *Nature* 382, 622–6.

De Vos, P., Lefebvre, A. M., Miller, S. G., Guerre-Millo, M., Wong, K., Saladin, R., Hamann, L. G., Staels, B., Briggs, M. R., and Auwerx, J. (1996). Thiazolidinediones repress ob gene expression in rodents via activation of peroxisome proliferator-activated receptor gamma. *J Clin Invest* 98, 1004–9.

Digby, J. E., Montague, C. T., Sewter, C. P., Sanders, L., Wilkison, W. O., O'Rahilly, S., and Prins, J. B. (1998). Thiazolidinedione exposure increases the expression of uncoupling protein 1 in cultured human preadipocytes. *Diabetes* 47, 138–41.

Elchebly, M., Payette, P., Michaliszyn, E., Cromlish, W., Collins, S., Loy, A. L., Normandin, D., Cheng, A., Himms-Hagen, J., Chan, C. C., Ramachandran, C., Gresser, M. J., Tremblay, M. L., and Kennedy, B. P. (1999). Increased insulin sensitivity and obesity resistance in mice lacking the protein tyrosine phosphatase-1B gene. *Science* 283, 1544–8.

Enerback, S., Jacobsson, A., Simpson, E. M., Guerra, C., Yamashita, H., Harper, M. E., and Kozak, L. P. (1997). Mice lacking mitochondrial uncoupling protein are cold-sensitive but not obese. *Nature* 387, 90–4.

Enerback, S., Ohlsson, B. G., Samuelsson, L., and Bjursell, G. (1992). Characterization of the human lipoprotein lipase (LPL) promoter: evidence of two cis-regulatory regions, LP-alpha and LP-beta, of importance for the differentiation-linked induction of the LPL gene during adipogenesis. *Mol Cell Biol* 12, 4622–33.

Fajas, L., Auboeuf, D., Raspe, E., Schoonjans, K., Lefebvre, A. M., Saladin, R., Najib, J., Laville, M., Fruchart, J. C., Deeb, S., Vidal-Puig, A., Flier, J., Briggs, M. R., Staels, B., Vidal, H., and Auwerx, J. (1997). The organization, promoter analysis, and expression of the human PPAR-gamma gene. *J Biol Chem* 272, 18779–89.

Fajas, L., Schoonjans, K., Gelman, L., Kim, J. B., Najib, J., Martin, G., Fruchart, J. C., Briggs, M., Spiegelman, B. M., and Auwerx, J. (1999). Regulation of peroxisome proliferator-activated receptor gamma expression by adipocyte differentiation and determination factor 1/sterol regulatory element binding protein 1: implications for adipocyte differentiation and metabolism. *Mol Cell Biol* 19, 5495–503.

Fleury, C., Neverova, M., Collins, S., Raimbault, S., Champigny, O., Levi-Meyrueis, C., Bouillaud, F., Seldin, M. F., Surwit, R. S., Ricquier, D., and Warden, C. H. (1997). Uncoupling protein-2: a novel gene linked to obesity and hyperinsulinemia [see comments]. *Nat Genet* 15, 269–72.

Forman, B. M., Tontonoz, P., Chen, J., Brun, R. P., Spiegelman, B. M., and Evans, R. M. (1995). 15-Deoxy-delta 12, 14-prostaglandin J2 is a ligand for the adipocyte determination factor PPAR gamma. *Cell* 83, 803–12.

Furumoto, T. A., Miura, N., Akasaka, T., Mizutani-Koseki, Y., Sudo, H., Fukuda, K., Maekawa, M., Yuasa, S., Fu, Y., Moriya, H., Taniguchi, M., Imai, K., Dahl, E., Balling, R., Pavlova, M., Gossler, A., and Koseki, H. (1999). Notochord-dependent expression of MFH1 and PAX1 cooperates to maintain the proliferation of sclerotome cells during the vertebral column development. *Dev Biol* 210, 15–29.

Ghorbani, M., Claus, T. H., and Himms-Hagen, J. (1997). Hypertrophy of brown adipocytes in brown and white adipose tissues and reversal of diet-induced obesity in rats treated with a beta3-adrenoceptor agonist. *Biochem Pharmacol* 54, 121–31.

Giacobino, J. P. (1995). Beta 3-adrenoceptor: an update. *Eur J Endocrinol* 132, 377–85.

Granneman, J. G., and Lahners, K. N. (1994). Analysis of human and rodent beta 3-adrenergic receptor messenger ribonucleic acids. *Endocrinology* 135, 1025–31.

Granneman, J. G., Lahners, K. N., and Chaudhry, A. (1991). Molecular cloning and expression of the rat beta 3-adrenergic receptor. *Mol Pharmacol* 40, 895–9.

Himms-Hagen, J. (1989). Brown adipose tissue thermogenesis and obesity. *Prog Lipid Res* 28, 67–115.

Himms-Hagen, J., Cui, J., Danforth, E., Jr., Taatjes, D. J., Lang, S. S., Waters, B. L., and Claus, T. H. (1994). Effect of CL-316,243, a thermogenic beta 3-agonist, on energy balance and brown and white adipose tissues in rats. *Am J Physiol* 266, R1371–82.

Hofmann, C., Lorenz, K., Braithwaite, S. S., Colca, J. R., Palazuk, B. J., Hotamisligil, G. S., and Spiegelman, B. M. (1994). Altered gene expression for tumor necrosis factor-alpha and its receptors during drug and dietary modulation of insulin resistance. *Endocrinology* 134, 264–70.

Holloway, B. R., Howe, R., Rao, B. S., and Stribling, D. (1992). ICI D7114: a novel selective adrenoceptor agonist of brown fat and thermogenesis. *Am J Clin Nutr* 55, 262S–264S.

Hotamisligil, G. S., Arner, P., Caro, J. F., Atkinson, R. L., and Spiegelman, B. M. (1995). Increased adipose tissue expression of tumor necrosis factor-alpha in human obesity and insulin resistance. *J Clin Invest* 95, 2409–15.

Hotamisligil, G. S., Shargill, N. S., and Spiegelman, B. M. (1993). Adipose expression of tumor necrosis factor-alpha: direct role in obesity-linked insulin resistance. *Science* 259, 87–91.

Iida, K., Koseki, H., Kakinuma, H., Kato, N., Mizutani-Koseki, Y., Ohuchi, H., Yoshioka, H., Noji, S., Kawamura, K., Kataoka, Y., Ueno, F., Taniguchi, M., Yoshida, N., Sugiyama, T., and Miura, N. (1997). Essential roles of the winged helix transcription factor MFH-1 in aortic arch patterning and skeletogenesis. *Development* 124, 4627–38.

Ito, M., Grujic, D., Abel, E. D., Vidal-Puig, A., Susulic, V. S., Lawitts, J., Harper, M. E., Himms-Hagen, J., Strosberg, A. D., and Lowell, B. B. (1998). Mice expressing human but not murine beta3-adrenergic receptors under the control of human gene regulatory elements. *Diabetes* 47, 1464–71.

Jezek, P., Orosz, D. E., Modriansky, M., and Garlid, K. D. (1994). Transport of anions and protons by the mitochondrial uncoupling protein and its regulation by nucleotides and fatty acids. A new look at old hypotheses. *J Biol Chem* 269, 26184–90.

Kaestner, K. H., Bleckmann, S. C., Monaghan, A. P., Schlondorff, J., Mincheva, A., Lichter, P., and Schutz, G. (1996). Clustered arrangement of winged helix genes fkh-6 and MFH-1: possible implications for mesoderm development. *Development* 122, 1751–8.

Kaestner, K. H., Christy, R. J., and Lane, M. D. (1990). Mouse insulin-responsive glucose transporter gene: characterization of the gene and trans-activation by the CCAAT/enhancer binding protein. *Proc Natl Acad Sci USA* 87, 251–5.

Kaestner, K. H., Lee, K. H., Schlondorff, J., Hiemisch, H., Monaghan, A. P., and Schutz, G. (1993). Six members of the mouse forkhead gene family are developmentally regulated. *Proc Natl Acad Sci USA* 90, 7628–31.

Kim, J. B., and Spiegelman, B. M. (1996). ADD1/SREBP1 promotes adipocyte differentiation and gene expression linked to fatty acid metabolism. *Genes Dev* 10, 1096–107.

Kim, J. B., Wright, H. M., Wright, M., and Spiegelman, B. M. (1998). ADD1/SREBP1 activates PPARgamma through the production of endogenous ligand. *Proc Natl Acad Sci USA* 95, 4333–7.

Klaus, S. (1997). Functional differentiation of white and brown adipocytes. *Bioessays* 19, 215–23.

Kopecky, J., Clarke, G., Enerback, S., Spiegelman, B., and Kozak, L. P. (1995). Expression of the mitochondrial uncoupling protein gene from the aP2 gene promoter prevents genetic obesity. *J Clin Invest* 96, 2914–23.

Kozak, L. P., Kozak, U. C., and Clarke, G. T. (1991). Abnormal brown and white fat development in transgenic mice overexpressing glycerol 3-phosphate dehydrogenase. *Genes Dev* 5, 2256–64.

Krief, S., Lonnqvist, F., Raimbault, S., Baude, B., Van Spronsen, A., Arner, P., Strosberg, A. D., Ricquier, D., and Emorine, L. J. (1993). Tissue distribution of beta 3-adrenergic receptor mRNA in man. *J Clin Invest* 91, 344–9.

Lafontan, M., and Berlan, M. (1993). Fat cell adrenergic receptors and the control of white and brown fat cell function. *J Lipid Res* 34, 1057–91.

Lean, M. E., James, W. P., Jennings, G., and Trayhurn, P. (1986). Brown adipose tissue uncoupling protein content in human infants, children and adults. *Clin Sci* 71, 291–7.

Lehmann, J. M., Moore, L. B., Smith-Oliver, T. A., Wilkison, W. O., Willson, T. M., and Kliewer, S. A. (1995). An antidiabetic thiazolidinedione is a high affinity ligand for, peroxisome proliferator-activated receptor gamma (PPAR gamma). *J Biol Chem* 270, 12953–6.

Lin, F. T., and Lane, M. D. (1992). Antisense CCAAT/enhancer-binding protein RNA suppresses coordinate gene expression and triglyceride accumulation during differentiation of 3T3-L1 preadipocytes. *Genes Dev* 6, 533–44.

Lin, F. T., and Lane, M. D. (1994). CCAAT/enhancer binding protein alpha is sufficient to initiate the 3T3-L1 adipocyte differentiation program. *Proc Natl Acad Sci USA* 91, 8757–61.

Loncar, D. (1991). Convertible adipose tissue in mice. *Cell Tissue Res* 266, 149–61.

Lopez, J. M., Bennett, M. K., Sanchez, H. B., Rosenfeld, J. M., and Osborne, T. E. (1996). Sterol regulation of acetyl coenzyme A carboxylase: a mechanism for coordinate control of cellular lipid. *Proc Natl Acad Sci USA* 93, 1049–53.

Lowell, B. B., V, S. S., Hamann, A., Lawitts, J. A., Himms-Hagen, J., Boyer, B. B., Kozak, L. P., and Flier, J. S. (1993). Development of obesity in transgenic mice after genetic ablation of brown adipose tissue. *Nature* 366, 740–2.

MacDougald, O. A., Cornelius, P., Lin, F. T., Chen, S. S., and Lane, M. D. (1994). Glucocorticoids reciprocally regulate expression of the CCAAT/enhancer-binding protein alpha and delta genes in 3T3-L1 adipocytes and white adipose tissue. *J Biol Chem* 269, 19041–7.

Mantzoros, C. S., Qu, D., Frederich, R. C., Susulic, V. S., Lowell, B. B., Maratos-Flier, E., and Flier, J. S. (1996). Activation of beta(3) adrenergic receptors suppresses leptin expression and mediates a leptin-independent inhibition of food intake in mice. *Diabetes* 45, 909–14.

Martin, G., Schoonjans, K., Lefebvre, A. M., Staels, B., and Auwerx, J. (1997). Coordinate regulation of the expression of the fatty acid transport protein and acyl-CoA synthetase genes by PPARalpha and PPARgamma activators. *J Biol Chem* 272, 28210–7.

Maslowska, M., Sniderman, A. D., Germinario, R., and Cianflone, K. (1997). ASP stimulates glucose transport in cultured human adipocytes. *Int J Obes Relat Metab Disord* 21, 261–6.

Miller, C. W., and Ntambi, J. M. (1996). Peroxisome proliferators induce mouse liver stearoyl-CoA desaturase 1 gene expression. *Proc Natl Acad Sci USA* 93, 9443–8.

Miura, N., Wanaka, A., Tohyama, M., and Tanaka, K. (1993). MFH-1, a new member of the fork head domain family, is expressed in developing mesenchyme. *FEBS Lett* 326, 171–6.§

Muzzin, P., Revelli, J. P., Kuhne, F., Gocayne, J. D., McCombie, W. R., Venter, J. C., Giacobino, J. P., and Fraser, C. M. (1991). An adipose tissue-specific beta-adrenergic receptor. Molecular cloning and down-regulation in obesity. *J Biol Chem* 266, 24053–8.

Nahmias, C., Blin, N., Elalouf, J. M., Mattei, M. G., Strosberg, A. D., and Emorine, L. J. (1991). Molecular characterization of the mouse beta 3-adrenergic receptor: relationship with the atypical receptor of adipocytes. *Embo J* 10, 3721–7.

Nicholls, D. G., and Locke, R. M. (1984). Thermogenic mechanisms in brown fat. *Physiol Rev* 64, 1–64.

Park, E. A., Roesler, W. J., Liu, J., Klemm, D. J., Gurney, A. L., Thatcher, J. D., Shuman, J., Friedman, A., and Hanson, R. W. (1990). The role of the CCAAT/enhancer-binding protein in the transcriptional regulation of the gene for phosphoenolpyruvate carboxykinase (GTP). *Mol Cell Biol* 10, 6264–72.

Peraldi, P., Xu, M., and Spiegelman, B. M. (1997). Thiazolidinediones block tumor necrosis factor-alpha-induced inhibition of insulin signaling. *J Clin Invest* 100, 1863–9.

Petruschke, T., and Hauner, H. (1993). Tumor necrosis factor-alpha prevents the differentiation of human adipocyte precursor cells and causes delipidation of newly developed fat cells. *J Clin Endocrinol Metab* 76, 742–7.

Pierrou, S., Hellqvist, M., Samuelsson, L., Enerback, S., and Carlsson, P. (1994). Cloning and characterization of seven human forkhead proteins: binding site specificity and DNA bending. *Embo J* 13, 5002–12.

Puigserver, P., Wu, Z., Park, C. W., Graves, R., Wright, M., and Spiegelman, B. M. (1998). A cold-inducible coactivator of nuclear receptors linked to adaptive thermogenesis. *Cell* 92, 829–39.

Rehnmark, S., Nechad, M., Herron, D., Cannon, B., and Nedergaard, J. (1990). Alpha- and beta-adrenergic induction of the expression of the uncoupling protein thermogenin in brown adipocytes differentiated in culture. *J Biol Chem* 265, 16464–71.

Ricquier, D., Bouillaud, F., Toumelin, P., Mory, G., Bazin, R., Arch, J., and Penicaud, L. (1986). Expression of uncoupling protein mRNA in thermogenic or weakly thermogenic brown adipose tissue. Evidence for a rapid beta-adrenoreceptor-mediated and transcriptionally regulated step during activation of thermogenesis. *J Biol Chem* 261, 13905–10.

Ross, S. R., Graves, R. A., Greenstein, A., Platt, K. A., Shyu, H. L., Mellovitz, B., and Spiegelman, B. M. (1990). A fat-specific enhancer is the primary determinant of gene expression for adipocyte P2 in vivo. *Proc Natl Acad Sci USA* 87, 9590–4.

Salmon, D. M., and Flatt, J. P. (1985). Effect of dietary fat content on the incidence of obesity among ad libitum fed mice. *Int J Obes* 9, 443–9.

Samuelsson, L., Stromberg, K., Vikman, K., Bjursell, G., and Enerback, S. (1991). The CCAAT/enhancer binding protein and its role in adipocyte differentiation: evidence for direct involvement in terminal adipocyte development. *EMBO J* 10, 3787–93.

Schoonjans, K., Peinado-Onsurbe, J., Lefebvre, A. M., Heyman, R. A., Briggs, M., Deeb, S., Staels, B., and Auwerx, J. (1 996). PPARalpha and PPARgamma activators direct a distinct tissue-specific transcriptional response via a PPRE in the lipoprotein lipase gene. *EMBO J* 15, 5336–48.

Sethi, J. K., and Hotamisligil, G. S. (1999). The role of TNF alpha in adipocyte metabolism. *Semin Cell Dev Biol* 10, 19–29.

Shimomura, I., Hammer, R. E., Richardson, J. A., Ikemoto, S., Bashmakov, Y., Goldstein, J. L., and Brown, M. S. (1998). Insulin resistance and diabetes mellitus in transgenic mice expressing nuclear SREBP-1c in adipose tissue: model for congenital generalized lipodystrophy. *Genes Dev* 12, 3182–94.

Soloveva, V., Graves, R. A., Rasenick, M. M., Spiegelman, B. M., and Ross, S. R. (1997). Transgenic mice overexpressing the beta 1-adrenergic receptor in adipose tissue are resistant to obesity. *Mol Endocrinol* 11, 27–38.

Susulic, V. S., Frederich, R. C., Lawitts, J., Tozzo, E., Kahn, B. B., Harper, M. E., Himms-Hagen, J., Flier, J. S., and Lowell, B. B. (1995). Targeted disruption of the beta 3-adrenergic receptor gene. *J Biol Chem* 270, 29483–92.

Tanaka, T., Yoshida, N., Kishimoto, T., and Akira, S. (1997). Defective adipocyte differentiation in mice lacking the C/EBPbeta and/or C/EBPdelta gene. *EMBO J* 16, 7432–43.

Tontonoz, P., Hu, E., Devine, J., Beale, E. G., and Spiegelman, B. M. (1995). PPAR gamma 2 regulates adipose expression of the phosphoenolpyruvate carboxykinase gene. *Mol Cell Biol* 15, 351–7.

Tontonoz, P., Hu, E., Graves, R. A., Budavari, A. I., and Spiegelman, B. M. (1994a). mPPAR gamma 2: tissue-specific regulator of an adipocyte enhancer. *Genes Dev* 8, 1224–34.

Tontonoz, P., Hu, E., and Spiegelman, B. M. (1994b). Stimulation of adipogenesis in fibroblasts by PPAR gamma 2, a lipid-activated transcription factor [published erratum appears in Cell 1995 Mar 24;80(6):following 957]. *Cell* 79, 1147–56.

Walsh, M. J., Sniderman, A. D., Cianflone, K., Vu, H., Rodriguez, M. A., and Forse, R. A. (1989). The effect of ASP on the adipocyte of the morbidly obese. *J Surg Res* 46, 470–3.

Wang, N. D., Finegold, M. J., Bradley, A., Ou, C. N., Abdelsayed, S. V., Wilde, M. D., Taylor, L. R., Wilson, D. R., and Darlington, G. J. (1995). Impaired energy homeostasis in C/EBP alpha knockout mice. *Science* 269, 1108–12.

Werman, A., Hollenberg, A., Solanes, G., Bjorbaek, C., Vidal-Puig, A. J., and Flier, J. S. (1997). Ligand-independent activation domain in the N terminus of peroxisome proliferator-activated receptor gamma (PPARgamma). Differential activity of PPARgamma1 and -2 isoforms and influence of insulin. *J Biol Chem* 272, 20230–5.

Wickelgren, I. (1998). Obesity: how big a problem? [news]. *Science* 280, 1364–7.

Winnier, G. E., Hargett, L., and Hogan, B. L. (1997). The winged helix transcription factor MFH1 is required for proliferation and patterning of paraxial mesoderm in the mouse embryo. *Genes Dev* 11, 926–40.

Wu, Z., Bucher, N. L., and Farmer, S. R. (1996). Induction of peroxisome proliferator-activated receptor gamma during the conversion of 3T3 fibroblasts into adipocytes is mediated by C/EBPbeta, C/EBPdelta, and glucocorticoids. *Mol Cell Biol* 16, 4128–36.

Wu, Z., Puigserver, P., Andersson, U., Zhang, C., Adelmant, G., Mootha, V., Troy, A., Cinti, S., Lowell, B., Scarpulla, R. C., and Spiegelman, B. M. (1999a). Mechanisms controlling mitochondrial biogenesis and respiration through the thermogenic coactivator PGC-1. *Cell* 98, 115–24.

Wu, Z., Rosen, E. D., Brun, R., Hauser, S., Adelmant, G., Troy, A. E., McKeon, C., Darlington, G. J., and Spiegelman, B. M. (1999b). Cross-regulation of C/EBP alpha and PPAR gamma controls the transcriptional pathway of adipogenesis and insulin sensitivity. *Mol Cell* 3, 151–8.

Wu, Z., Xie, Y., Bucher, N. L., and Farmer, S. R. (1995). Conditional ectopic expression of C/EBP beta in NIH-3T3 cells induces PPAR gamma and stimulates adipogenesis. *Genes Dev* 9, 2350–63.

Yeh, W. C., Cao, Z., Classon, M., and McKnight, S. L. (1995). Cascade regulation of terminal adipocyte differentiation by three members of the C/EBP family of leucine zipper proteins. *Genes Dev* 9, 168–81.

Yubere, P., Manchado, C., Cassard-Doulcier, A. M., Mampel, T., Vinas, O., Iglesias, R., Giralt, M., and Villarroya, F. (1994). CCAAT/enhancer binding proteins alpha and beta are transcriptional activators of the brown fat uncoupling protein gene promoter. *Biochem Biophys Res Commun* 198, 653–9.

Zhang, Y., Proenca, R., Maffei, M., Barone, M., Leopold, L., and Friedman, J. M. (1994). Positional cloning of the mouse obese gene and its human homologue [published erratum appears in Nature 1995 Mar 30;374(6521):479]. *Nature* 372, 425–32.

What is claimed is:

1. A construct comprising an adipose-specific promoter operably linked to a nucleotide sequence encoding a polypeptide comprising the amino acid sequence of SEQ ID NO:2.

2. The construct according to claim 1, wherein the adipose-specific promoter is the promoter of the murine gene encoding adipocyte P2.

3. The construct according to claim 1, wherein the nucleotide sequence comprises SEQ ID NO:1.

4. A vector comprising a construct according to claim 1.

5. The construct of claim 1, further comprising an adipose-specific enhancer.

6. The vector of claim 4, wherein the vector is a viral vector.

7. The vector of claim 6, wherein the viral vector is an adenoviral, adeno-associated, or retroviral vector.

8. A construct comprising an adipose-specific promoter operably linked to a nucleotide sequence that is at least 95% identical to SEQ ID NO:1, wherein the nucleotide sequence encodes a polypeptide that down regulates the activity of the Ob promoter.

9. The construct of claim 8, wherein the adipose-specific promoter is the promoter of the murine gene encoding adipocyte P2.

10. The construct of claim 8, further comprising an adipose-specific enhancer.

11. A vector comprising the construct of claim 8.

12. The vector of claim 11, wherein the vector is a viral vector.

13. The vector of claim 12, wherein the viral vector is an adenoviral, adeno-associated, or retroviral vector.

* * * * *